United States Patent
Vegas et al.

(10) Patent No.: US 10,842,753 B2
(45) Date of Patent: *Nov. 24, 2020

(54) MODIFIED ALGINATES FOR CELL ENCAPSULATION AND CELL THERAPY

(71) Applicants: Massachusetts Institute of Technology, Cambridge, MA (US); The Children's Medical Center Corporation, Boston, MA (US)

(72) Inventors: Arturo J. Vegas, Belmont, MA (US); Minglin Ma, Ithaca, NY (US); Kaitlin M. Bratlie, Ames, IA (US); Daniel G. Anderson, Framingham, MA (US); Robert S. Langer, Newton, MA (US)

(73) Assignees: Massachusetts Institute of Technology, Cambridge, MA (US); The Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,899

(22) Filed: May 10, 2019

(65) Prior Publication Data

US 2019/0262272 A1 Aug. 29, 2019

Related U.S. Application Data

(63) Continuation of application No. 15/588,481, filed on May 5, 2017, now Pat. No. 10,292,936, which is a continuation of application No. 15/208,192, filed on Jul. 12, 2016, now Pat. No. 10,285,949, which is a continuation of application No. 13/487,524, filed on Jun. 4, 2012, now Pat. No. 9,422,373.

(60) Provisional application No. 61/492,705, filed on Jun. 2, 2011.

(51) Int. Cl.
| A61K 9/50 | (2006.01) |
| A61K 9/00 | (2006.01) |
| C08B 37/00 | (2006.01) |
| A61K 35/39 | (2015.01) |
| A61K 45/06 | (2006.01) |
| A61K 9/51 | (2006.01) |

(52) U.S. Cl.
CPC .......... *A61K 9/5036* (2013.01); *A61K 9/0024* (2013.01); *A61K 35/39* (2013.01); *A61K 45/06* (2013.01); *C08B 37/0084* (2013.01); *A61K 9/5161* (2013.01)

(58) Field of Classification Search
None
See application file for complete search history.

(56) References Cited

U.S. PATENT DOCUMENTS

| 2,881,161 | A | 4/1959 | Kohler |
| 4,352,883 | A | 10/1982 | Lim |
| 2,860,130 | A | 11/1985 | McNeely |
| 5,336,668 | A | 8/1994 | dellaValle |
| 5,443,505 | A | 8/1995 | Wong |
| 5,622,718 | A | 4/1997 | Al-Shamkhani |
| 5,876,452 | A | 3/1999 | Athanasiou |
| 6,159,531 | A | 12/2000 | Dang |
| 6,440,940 | B1 | 8/2002 | Doyle |
| 7,008,476 | B2 | 3/2006 | Wu |
| 2004/0253532 | A1 | 12/2004 | Wu |
| 2008/0044900 | A1 | 2/2008 | Mooney |
| 2008/0199914 | A1 | 8/2008 | Skjak-Braek |
| 2008/0242738 | A1 | 10/2008 | Marks |
| 2008/0268189 | A1 | 10/2008 | Sun |
| 2009/0148591 | A1 | 6/2009 | Wang |
| 2009/0148597 | A1 | 6/2009 | Wang |
| 2012/0009159 | A1 | 1/2012 | Humayun |
| 2012/0083767 | A1 | 4/2012 | Gerstenblith |
| 2012/0282299 | A1 | 11/2012 | Delamarre |
| 2013/0224276 | A1 | 8/2013 | Hunter |

FOREIGN PATENT DOCUMENTS

| CN | 101565469 | 10/2009 |
| DE | 102005049833 | 4/2007 |
| EP | 0493265 | 7/1991 |
| EP | 1614696 | 1/2006 |
| FR | 2699545 | 6/1994 |
| GB | 768309 | 2/1957 |
| WO | 8603781 | 7/1986 |
| WO | 9900070 | 1/1999 |
| WO | 2003/010354 | 2/2003 |
| WO | 2003010354 | 2/2003 |
| WO | 03/085372 | 10/2003 |
| WO | 03085372 | 10/2003 |
| WO | 2005/058382 | 6/2005 |
| WO | 2005058382 | 6/2005 |

(Continued)

OTHER PUBLICATIONS

Chen, "Differentiation of rat marrow mesenchymal stem cells into pancreatic islet beta-cells", *World Journal of Gastroenterology*, 10(20): 3016-3020 (2004).

Costa, et al., "Covalent immobilization of antimicrobial peptides (AMPs) onto biomaterial surfaces", *Acta Biomaterialia*, 7(5): 1431-1440 (2010).

DeVos, et al., "Improved biocompatibility but limited graft survival after purification of alginate for microencapsulation of pancreatic islets", *Diabetologia*, 40(3):262-270 (1997).

(Continued)

*Primary Examiner* — Layla D Berry
(74) *Attorney, Agent, or Firm* — Pabst Patent Group LLP

(57) ABSTRACT

Covalently modified alginate polymers, possessing enhanced biocompatibility and tailored physiochemical properties, as well as methods of making and use thereof, are disclosed herein. The covalently modified alginates are useful as a matrix for the encapsulation and transplantation of cells. Also disclosed are high throughput methods for the characterizing the biocompatibility and physiochemical properties of modified alginate polymers.

20 Claims, 6 Drawing Sheets

(56) References Cited

FOREIGN PATENT DOCUMENTS

| | | |
|---|---|---|
| WO | 2005/063147 | 7/2005 |
| WO | 2005063147 | 7/2005 |
| WO | 2009/032158 | 3/2009 |
| WO | 2009032158 | 3/2009 |
| WO | 2010/090767 | 8/2010 |
| WO | 2010090767 | 8/2010 |
| WO | 2013/121983 | 8/2013 |
| WO | 2013121983 | 8/2013 |

OTHER PUBLICATIONS

Hudalla, et al., "Immobilization of peptides with distinct biological activities onto stem cell culture substrates using orthogonal chemistries", Langmuir, 26(9):6449-6456 (2010).

Lee, et al., "Development and characterization of an alignate-impregnated polyester vascular graft", Journal of Biomedical Materials Research, 36(2):200-208 (1997).

Tang, et al., "Reprogramming liver-stem WB fcells into functional insulin-prodcuing cells by persistent expression of Pdx1-and Pdx1-VP16 mediated by lentiviral vectors", Lab Invest., 86(1)83-93 (2006).

Thevenot, et al., "Surface chemistry influences implant biocompatibility", Curr. Top Med. Chem.,. 8(4):270-80 (2011).

Vallee, et al., "Synthesis and rheological properties of hydrogels based on amphiphilic alginate-amide derivatives", Carbohydrate Res., 344:223-8 (2009).

Kovach, et al., "The Effects of PEG-based surface modification of PDMS microchannels on long-term hemocompatibility", J. of Biomedical Research Pt. A, 102A:4195-4205 (2014).

Ratner, "A pore way to heal and regenerate: 21st century thinking on biocompatibility", Regenerative Biomaterials, 107-110 (2016).

Chen, et al., "Multifunctional Biocompatible Membrane and Its Application to Fabricate a Miniaturized Glucose Sensor with Potential for Use in Vivo", Biomedical Microdevices, 1(2):155-166 (1998).

Chu, et al., "A soft and flexible biosensor using a phospholipid polymer for continuous glucose monitoring", Biomedical Microdevices, 11(4):837-842 (2009).

Cui, et al., "Electrochemical deposition and characterization of poly (3, 4-ethylenedioxythiophen) on neural microelectrode arrays", Sensors and Actuators B, 89:92-102 (2003).

Hersel, et al., "RGD modified polymers: biomaterials for stimulated cell adhesion and beyond", Biomaterials, 24(24):4385-4415 (2003).

Huh, et al., "From 3D cell culture to organs-on chips", Trends in Cell Biology, 21(12):745-754 (2011).

West, et al., "The biocompatibility of crosslinkable copolymer coatings containing sulfobetaines and phosphobetaines", Biomaterials, 25(7-8):1195-1204 (2004).

Yang, et al., "Zwitterionic poly(carboxybetaine) hydrogels for gluclose biosensors in complex media", Biosensors and Bioelectronics, 26(5):2454-2459 (2011).

Extended European Search Report issued for EP 18 16 2427 dated Jun. 19, 2018.

Dusseault, et al., "Evaluation of alginate purification methods: Effect on polyphenol, endotoxin, and protein contamination", J Biomed Mater Res., 76(2(:243-51 (2006).

Gattas-Asfura, et al., "Chemoselective cross-linking anddunctionalization of alginate via Staudinger ligation", Biomacromole., 10:3122-29 (2009).

Hall, at al., "Microencapsulation of islets within alginate/ poly)ethyiene glycol) gels cross-linked via Staudinger ligation", Acta Biomaterialia, 7:614-24 (2011).

Klock, at al., "Production of purified alginates suitable for use in immunoisolated transplantation", Appl Microbiol Biotechnol., 40:638-43 (1994).

Babak, et al., "Hydrophobically Associating Alginate Derivatives: Surface Tension Properties of Their Mixed Aqueous Solutions with Oppositely Charged Sufactants", J Colloid Interface Sci., 225(2):505-10 (2000).

Bloch, et al., "Improved activity of streptozotocin-selected insulinoma cells following microencapsulation and transplantation into diabetic mice", Cell Biol Int.,30(2):138-43 (2006).

Bratlie, et al., "Rapid biocompatibility analysis of materials via in vivo fluorescence Imaging of mouse models", PLoS one, 5(4):e10032 (2010).

Breger, "Comparison of ionically and novel covalently crosslinked alginate microspheres", AICHE annual meeting, Nashville Tn. (2009).

Brodkorb, "Alginate", Bioencapsulation Encylopedia,#252 (2009).

Brodrick, et al., "The characterisation of a novel, covalently modified, amphiphllo alginate derivative, which retains gelling and non-toxic properties", J Colloid Interface Sci., 298(1):154-61(2006).

Chitnis and Ohman, "Cloning of Pseudomonas aerugincsa algG, which controls alginate structure", J Bacteriol, 172(6):2894-2900 (1900).

Cheung, et al., "A critical review on polymer-based bio-engineered materials for scalfold development", Comp. Part B Eng., 38:291-300 (2007).

Choudhary, et al., "Hydrophobically modified alginate for drug delivery systems", Bioengineering Conference, 35th Annual Northeat Meeting, Apr. 3-5, (2009).

Coleman, et al., "Phosphorylation of alginate: synthesis, characterization, and evaluation of in vitro mineralization capacity", Biomacromolecules, 12(4):889-97 (2011).

De Vos, et al., "Alginate-based microcapsules for Immunoisolation of pancreatic islets", Biomaterials, 27(32):5603-17 (2006).

Denev, et al., "Synthesis and characteristics of alginate amides", EJEAFChe., 4(6):1143-9 (2005).

Drury and Mooney, "Hydrogels for tissue engineering: scaffold design variables and applications", Biomaterials, 24:4337-51 (2003).

Elliot, et al., "Live encapsulated porcine islets from a type 1 diabetic patient 9.5 yr after xenotransplantation", Xenotransplatation, 14(2):157-61 (2007).

FMC Biopolymer, "Alginates", http://fmcbiopolymer.com , accessed Apr. 4, 2011.

FMC Biopolymer, "Propylene Glycol Alginate", http://www.fmcbiopolymer.com, accessed Apr. 4, 2011.

Gomez, et al., "Oxidation of sodium alginate and characterization of the oxidized derivatives", Carbohydrate Polymers, 67(3):296-304 (2007).

Hassan, "Present Stalus in the Chemistry of Hexuronic Acids Found in Glycosaminoglycans and their Mimetic Aza-Sugars Analogues", Mini-Rev Org Chem., 4:61-74 (2007).

Hughson, "Entrapment of micro-algae in modified alginate beads of oxygen and nutrient source", Oregon State University, presented Mar. 16, (2005).

Kolb, et al., "Click Chemistry: Diverse Chemical Function from a Few Good Reactions", Angew Chen Int Ed., 40:2004-21 (2001).

Kolb and Sharpless, "The growing impact of click chemistry on drug discovery", Drug Discov Today, 8(24):1128-37 (2003).

Le-Tien, et al., "Modified alginate and chilosen for lactic acid bacteria immobilization", Biotechnol Appl Biochem., 39:347-54 (2004).

Leonard, et al., "Hydrophobically modified alginate hydrogels as protein carriers with specific controlled release properties", J Control Release, 98(3):395-495 (2004).

Lim and Sun, "Microencapsulated islets as bioartificial endocrine pancreas", Science, 210:908-10 (1980).

Pindar and Bucke, "The biosynthesis of alginic acid by Azotobacter vinelandii", Biochem J., 152:617-22 (1975).

Pelletier, et al., "Amphiphilic derivatives of sodium alginate and hyaluronate: synthesis and phsico-chemical properties of aqueous dilute soluations", Carbohydrate Polymers, 43(4):343-9 (2000).

Pourjavadi, et al., "Partially hydrolyzed crosslinked aiginate-gradd-polymethacrylamide as a novel biopolymer-based superabsorbent hydrogel having pri-responsive Properties", Macromolecular Research, 13(1):45-53 (2005).

Rokstad, et al., "Cell-compatible covalently reinforced beads obtained from a chemoenzymatically engineered alginate", Biomaterials, 27(27):4726-37 (2006).

(56) References Cited

OTHER PUBLICATIONS

Ronghua, et al., "Preparation and in vitro antcoagulant activities of alginate sulfats and its quaterized derivatives", Carbohydrate POlymers, 52(1):19-24(2003).
Yang, et al., "Amphiphilic cholesteryl grafted sodium alginate derivative: Synthesis and self-assembly in aqueous solution", Carbohydrate Polymers, 68(2):218-25 (2007).
Yang, et al., "Research progress on chemical modification of alginate: A review", Carbon. Polyn., 84(1):33-9 (2011).
Dusseault, "Evaluation of alginate purification methods: effect on polyphenol, endotoxin, and protein contamination", J Biomed Mater Res A., 76(2):243-251 (2006).
Yang, et al., "Zwitterionic poly (carboxybetaine) hydrogels for glucose biosensors in complex media", *Biosensors and Bioelectronics*, 26(5):2454-2459 (2011).
Ratner, "A pore way to heal and regenerate: 21st century thinking on biocompatibility", *Regenerative Biomaterials*, 1074-110 (2016).

MODIFIED ALGINATES FOR CELL ENCAPSULATION AND CELL THERAPY

CROSS REFERENCE TO RELATED APPLICATIONS

This application is a continuation of U.S. application Ser. No. 15/588,481, filed May 5, 2017, which is a continuation of U.S. application Ser. No. 15/208,192, filed Jul. 12, 2016, which is a continuation of U.S. application Ser. No. 13/487,524, filed Jun. 4, 2012, now U.S. Pat. No. 9,422,373, issued Aug. 23, 2016, which claims priority and benefit to U.S. Provisional Application No. 61/492,705, filed Jun. 2, 2011, by Arturo J. Vegas, Kaitlin M. Bratlie, Daniel G. Anderson, and Robert S. Langer, the disclosures of which are hereby incorporated herein by reference in their entirety.

STATEMENT REGARDING FEDERALLY SPONSORED RESEARCH OR DEVELOPMENT

This invention was made with Government Support under Grant No. R01 DE016516 awarded by the National Institutes of Health. The Government has certain rights in the invention.

FIELD OF THE INVENTION

The present invention relates to the use of alginates, chemically modified to enhance their biocompatibility and tailor their physical properties, for the encapsulation of cells, particularly for the encapsulation of pancreatic islet cells, as well as methods of treating diseases or disorders, including diabetes, by implantation of the encapsulated cells.

BACKGROUND OF THE INVENTION

The transplantation of hormone- or protein-secreting cells from genetically non-identical members of the same species (i.e. allotransplantation) or from other species (i.e. xenotransplantion) is a promising strategy for the treatment of many diseases and disorders. Using alginate microcapsules to provide immunoisolation, hormone- or protein-secreting cells can be transplanted into a patient without the need for extensive treatment with immunosuppressant drugs. This principle has been successfully demonstrated by the transplantation of alginate-encapsulated pancreatic β-cells in diabetic rat models (Lim, F. and Sun, A. M. *Science*. 210, 908-910 (1980)). Methods of encapsulating biological material in alginate gels are described, for example, in U.S. Pat. No. 4,352,883 to Lim. In the Lim process, an aqueous solution containing the biological materials to be encapsulated is suspended in a solution of a water soluble polymer. The suspension is formed into droplets which are configured into discrete microcapsules by contact with multivalent cations such as $Ca^{2+}$. The surface of the microcapsules is subsequently crosslinked with polyamino acids, forming a semipermeable membrane around the encapsulated materials.

The Lim method employs conditions which are mild enough to encapsulate cells without adversely affecting their subsequent survival and function. The resulting alginate microcapsules are semipermeable, possessing sufficient porosity to permit nutrients, waste, and the hormones and/or proteins secreted from encapsulated cells to diffuse freely into and out of the microcapsules, and, when implanted into an animal host, the alginate microcapsules effectively isolate the encapsulated cells from the host's immune system. See also U.S. Pat. No. 7,807,150 to Vacanti, et al.

Many other synthetic materials have been tried, including block copolymers such as polyethyleneglycol-diacrylate polymers, polyacrylates, and thermoplastic polymers, as reported by U.S. Pat. No. 6,129,761 to Hubbell and by Aebischer, et al, *J Biomech Eng.* 1991 May; 113(2):178-83. See Lesney Modern Drug Discovery 4(3), 45-46, 49, 50 (2001) for review of these materials.

Since Lim first reported on the transplantation of encapsulated cells, many other have tried to create "bioreactors" for cells that could maintain viability of the cells in the absence of vascularization, by diffusion of nutrients, gases and wastes through the encapsulating materials, and still protect the cells from the body's immune defenses against foreign cells and materials. Unfortunately, efforts to translate these therapies into human subjects have proven difficult. For example, alginate-encapsulated porcine islet cells transplanted into a human subject suffering from Type 1 diabetes initially demonstrated significant improvement and required decreased insulin dosing. However, by week 49, the patient's insulin dose retuned to pre-transplant levels (Elliot, R. B. et al. *Xenotransplantation.* 2007; 14(2): 157-161).

In some cases, it is desirable to elicit fibrosis, for example, when the cells are implanted as a bulking material, as described in U.S. Pat. No. 6,060,053 and as subsequently approved by the Food and Drug Administration for treatment of vesicoureteral reflux.

The diminished efficacy of the implanted cells over time is the result of fibroblastic overgrowth of the alginate capsules. The alginate gel matrix provokes an inflammatory response upon implantation, resulting in the encapsulation of the alginate matrix with fibrous tissue. The fibrous tissue on the alginate capsule surface reduces the diffusion of nutrients and oxygen to the encapsulated cells, causing them to die. No better results have been obtained with the other materials.

Therefore, it is an object of the invention to provide polymers suitable for encapsulation and implantation of cells where the polymers have greater long term biocompatibility following implantation.

It is another object of the present invention to provide chemically modified, ionically crosslinkable alginates with improved biocompatibility and tailored physiochemical properties, including gel stability, pore size, and hydrophobicity/hydrophilicity.

It is also an object of the invention to provide methods for the encapsulation of cells using modified alginate polymers.

It is a further object of the invention to provide methods for treating a disorder or disease in a human or animal patient by transplanting exogenous biological material encapsulated in a modified alginate polymer.

Finally, it is an object of the invention to provide high-throughput methods for the characterization of modified alginate polymers.

SUMMARY OF THE INVENTION

Alginates, chemically modified to tailor their biocompatibility and physical properties, have been developed. The modified alginates described herein provide enhanced properties relative to unmodified alginates. Moreover, based on the discovery that the starting materials, as well as chemically modified and reacted materials, must be exhaustively purified to remove contaminants prior to implantation to prevent encapsulation, these materials are less likely to elicit fibrous capsule formation following implantation.

Modified alginates are alginate polymers that contain one or more covalently modified monomers defined by Formula I

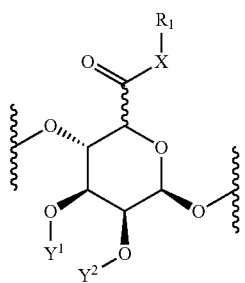

Formula I wherein,

X is oxygen, sulfur, or NR;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

$Y_1$ and $Y_2$ independently are hydrogen or —PO(OR)$_2$; or $Y_2$ is absent, and $Y_1$, together with the two oxygen atoms to which $Y_1$ and $Y_2$ are attached form a cyclic structure as shown below

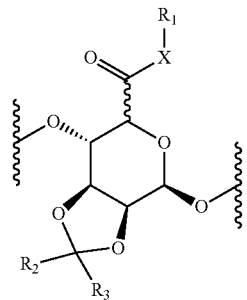

wherein n is an integer between 1 and 4; and $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and R is, independently for each occurrence, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

Modified alginates can be either singularly modified alginate polymers or multiply modified alginate polymers. Singularly modified alginate polymers are alginate polymers that contain one or more covalently modified monomers, wherein substantially all of the covalently modified monomers possess the same covalent modification (i.e. the polymer contains one 'type' or species of covalently modified monomer). Multiply modified alginate polymers are alginate polymers that contain covalently modified monomers, wherein substantially all of the covalently modified monomers do not possess the same covalent modification (i.e. the polymer contains two or more 'types' or species of covalently modified monomers).

In some embodiments, the modified alginate polymer is a singularly modified alginate polymer. In preferred embodiments, the modified alginate polymer is a multiply modified alginate polymer possessing a polysaccharide backbone containing mannuronate monomers, guluronate monomers, a first species or type of covalently modified monomer defined by Formula I, and a second species or type of covalently modified monomer defined by Formula I. In some embodiments, the modified alginate polymer is one of the multiply modified alginate polymers shown below.

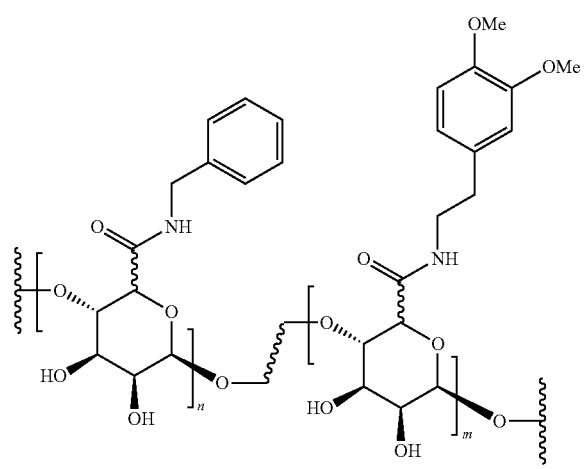
PF_N263_A7
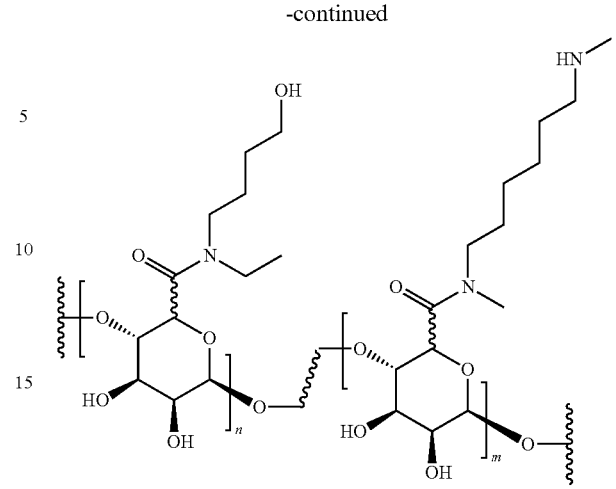
PF_N263_C12
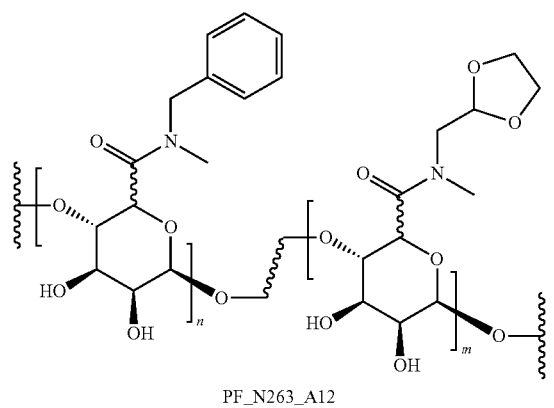
PF_N263_A12
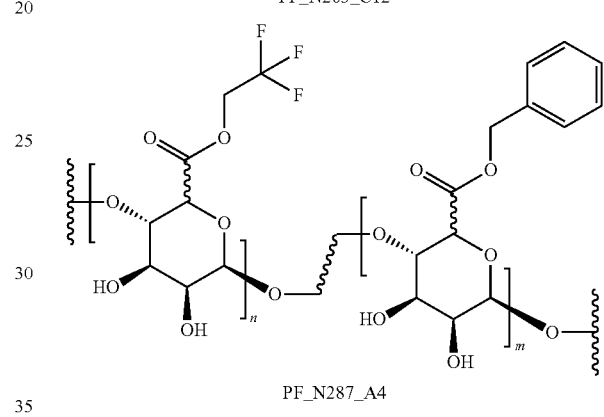
PF_N287_A4
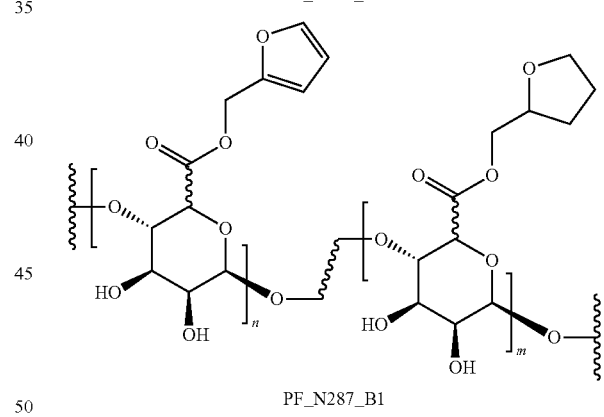
PF_N287_B1
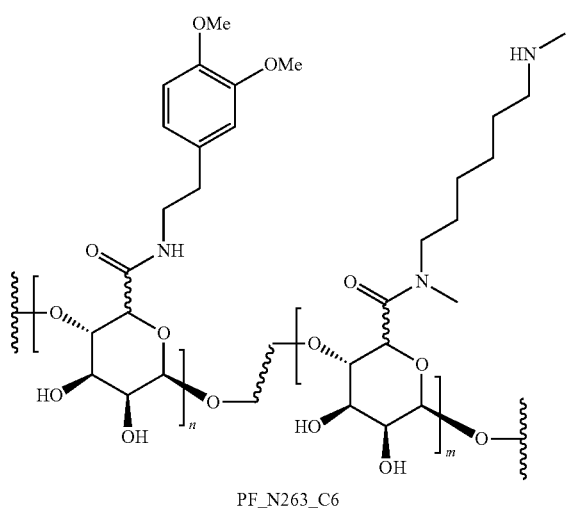
PF_N263_C6
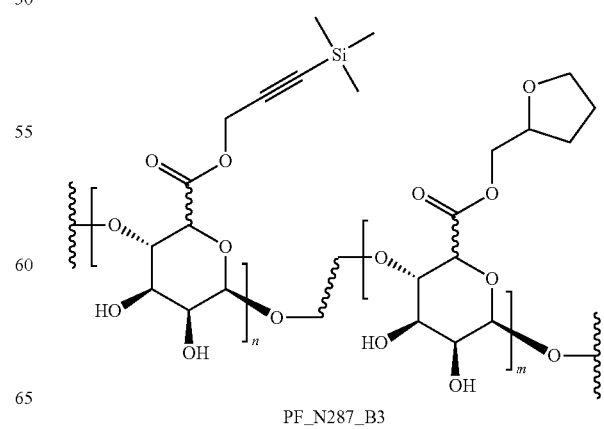
PF_N287_B3

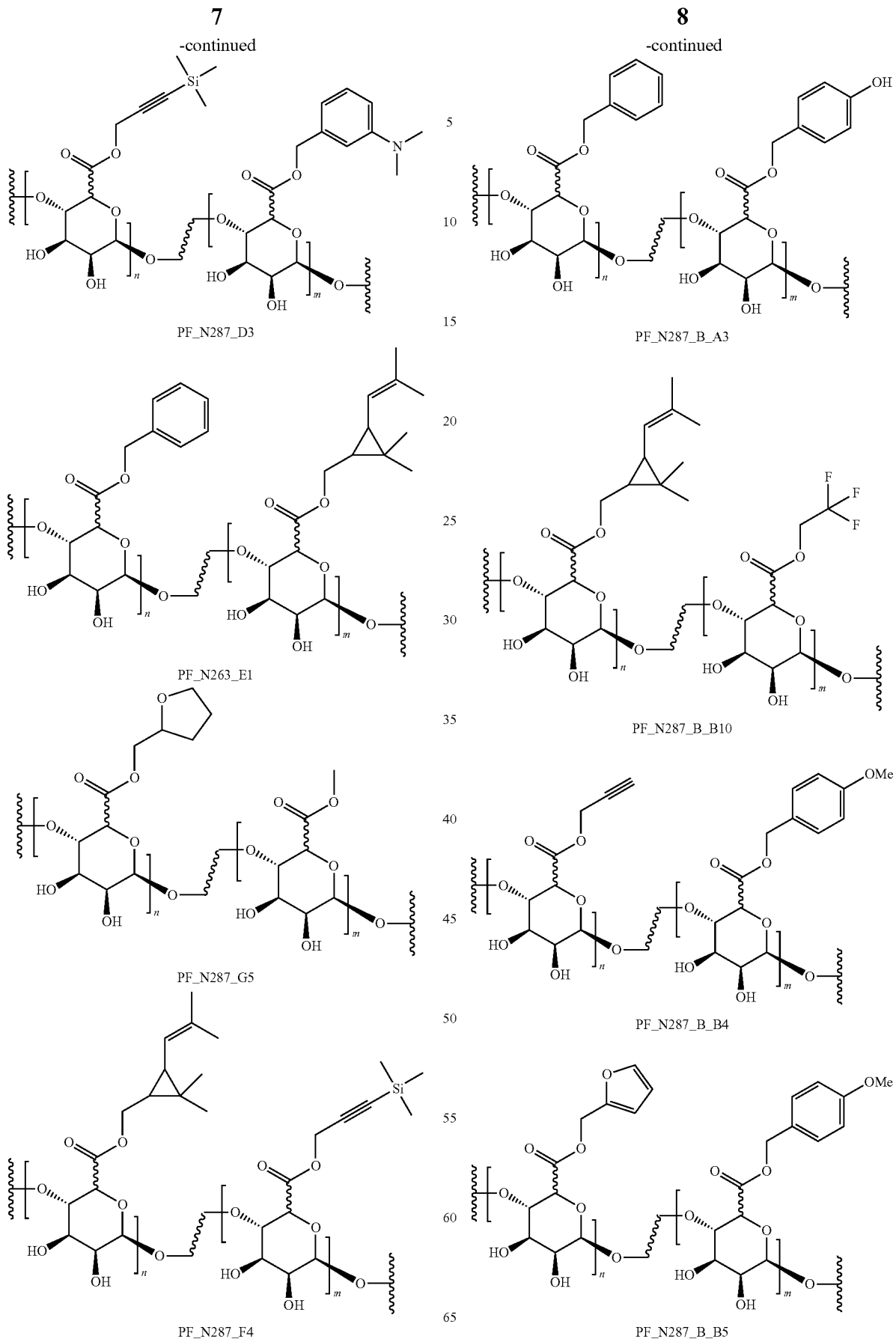

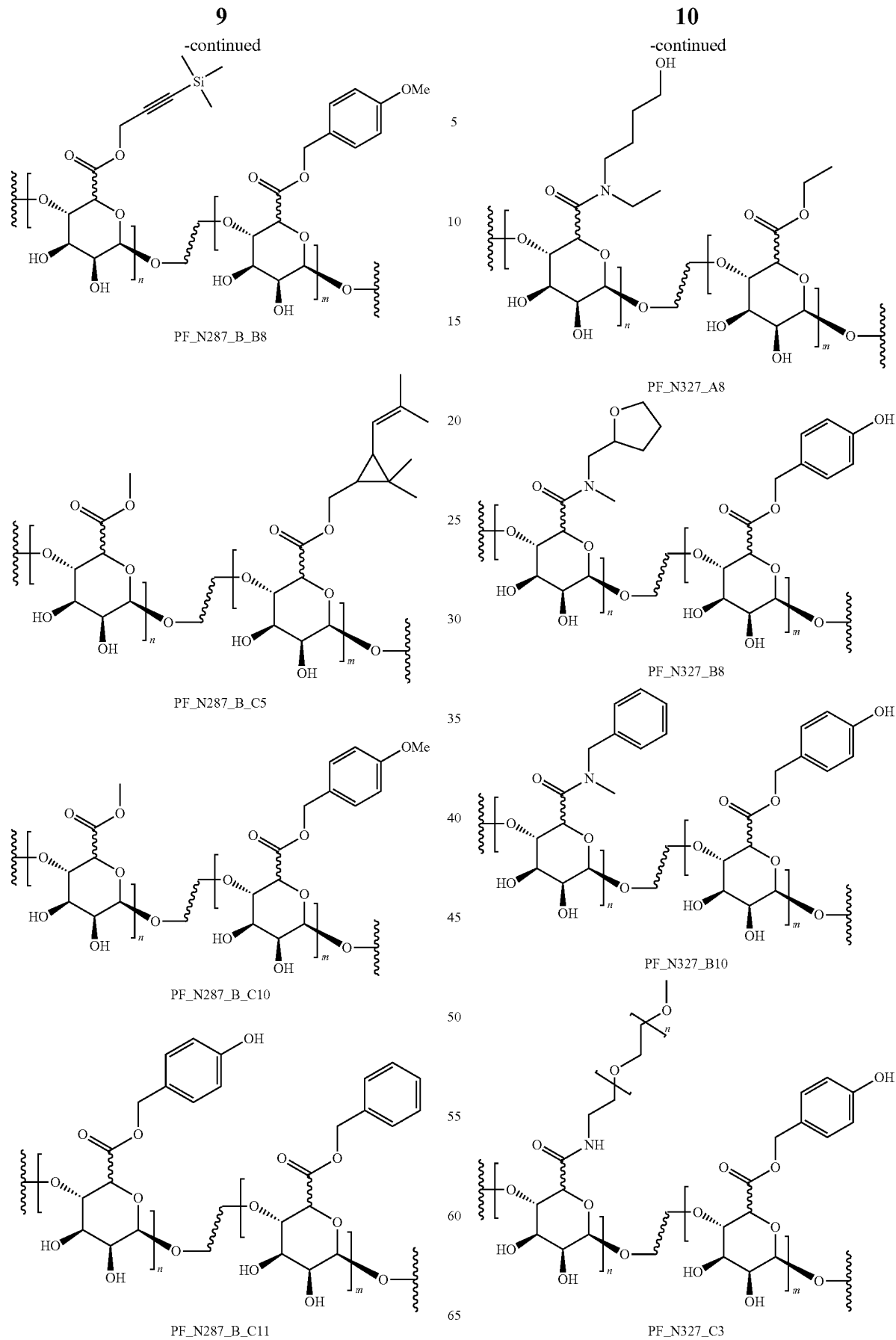

-continued

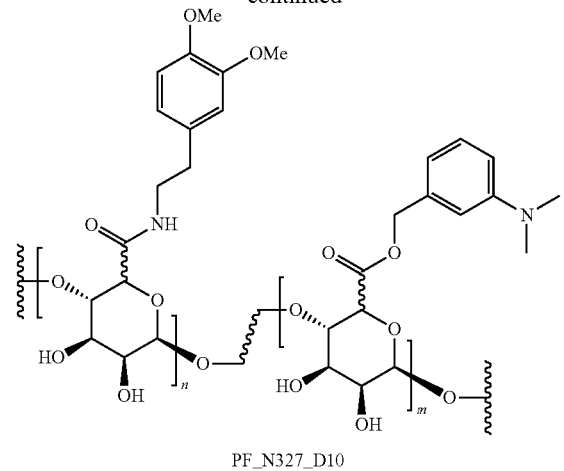

PF_N327_D10

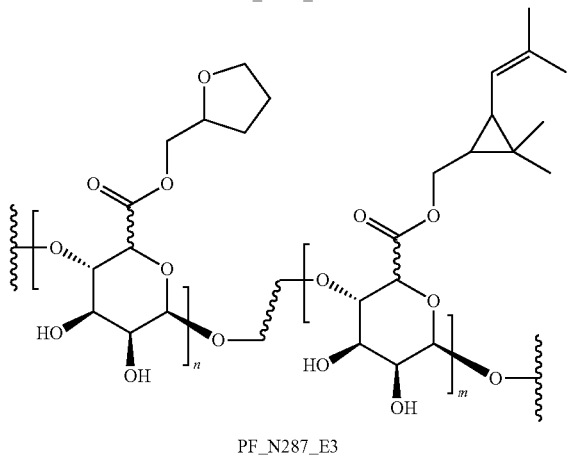

PF_N287_E3

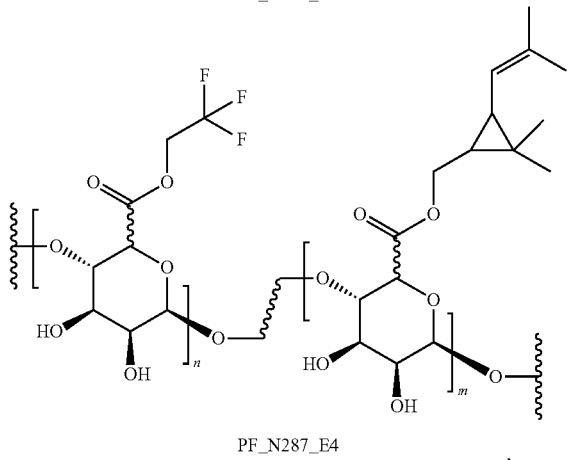

PF_N287_E4

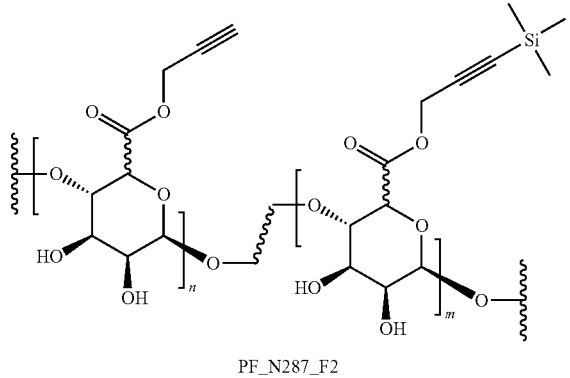

PF_N287_F2

Modified alginate polymers can contain any ratio of mannuronate monomers, guluronate monomers, and covalently modified monomers. In preferred embodiments, greater than 20%, more preferably greater than 25%, and most preferably greater than 30%, of the monomers in the modified alginate polymer are covalently modified monomers.

In preferred embodiments, the modified alginate polymer can be ionically crosslinked to form hydrogels using a polyvalent ion, such as $Ca^{2+}$, $Sr^{2+}$, or $Ba^{2+}$. The ability of modified alginates to form stable hydrogels in physiological conditions can be quantified using the hydrogel formation assay described herein. In preferred embodiments, the modified alginate polymer forms hydrogels such that the fluorescence intensity measured using the high throughput assay described herein is between 15,000 and 55,000, preferably between 20,000 and 55,000, more preferably between 25,000 and 55,000.

In preferred embodiments, the modified alginate is biocompatible, and induces a lower foreign body response than unmodified alginate. The biocompatibility of modified alginates can be quantitatively determined using in vitro and in vivo assays known in the field, including the in vivo biocompatibility assay described herein. In preferred embodiments, the modified alginate polymer is biocompatible such that the fluorescence response normalized to unmodified alginate measured using the in vivo biocompatibility assay described herein is less than 75%, 70%, 65%, 60%, 55%, or 50%. Also described are assays for the characterization of modified alginate polymers.

A high throughput assay useful to characterize the ability of modified alginate polymers to form hydrogels is also described. In some embodiments, the hydrogel formation assay described herein is used to quantify the stability of hydrogels formed from alginates or modified alginates. In preferred embodiments, the hydrogel formation assay described herein is used as a screening tool to identify modified alginates capable of forming stable hydrogels. The high throughput in vivo biocompatibility assay described herein is used to identify modified alginates which induce a lower foreign body response than unmodified alginate. Assays are also provided for quantifying the biocompatibility of modified alginates.

Further described herein are methods of encapsulating biological materials using modified alginate polymers. In particular embodiments, the modified alginate polymers described herein are used to encapsulate cells for use in methods of treating a disease or disorder in a human or animal patient. In some embodiments, a disease or disorder in a human or animal patient is treated by transplanting exogenous biological material encapsulated in a modified alginate polymer. In particular embodiments, a disease or disorder in a human or animal patient is treated by transplanting cells encapsulated in a modified alginate polymer. In a more particular embodiment, diabetes is treated by transplanting pancreatic islet cells encapsulated in a modified alginate polymer.

Modified alginates yielding fluorescence values below 15,000 were considered unusable for applications where hydrogel formation is critical (i.e. the encapsulation of cells).

Figure 3:
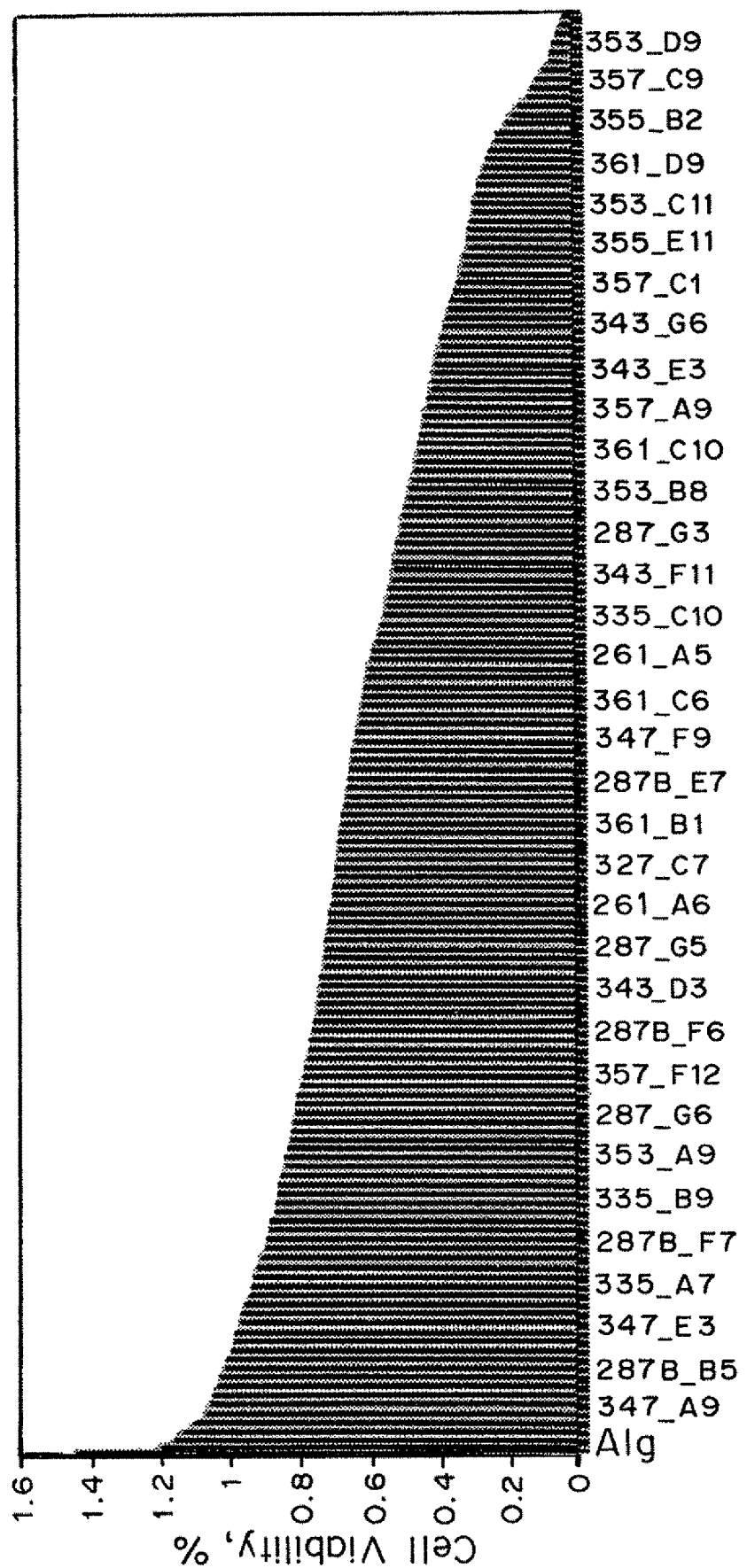

FIG. 3 is a plot showing the effect of selected modified alginates on HeLa cell line viability as compared to the positive control (no alginate). Alginate (Alg) has a viability of 53%. Several polymers are shown to be more cytotoxic than Alg, however, the majority of the library performs as well or better than Alg.

Figure 4:
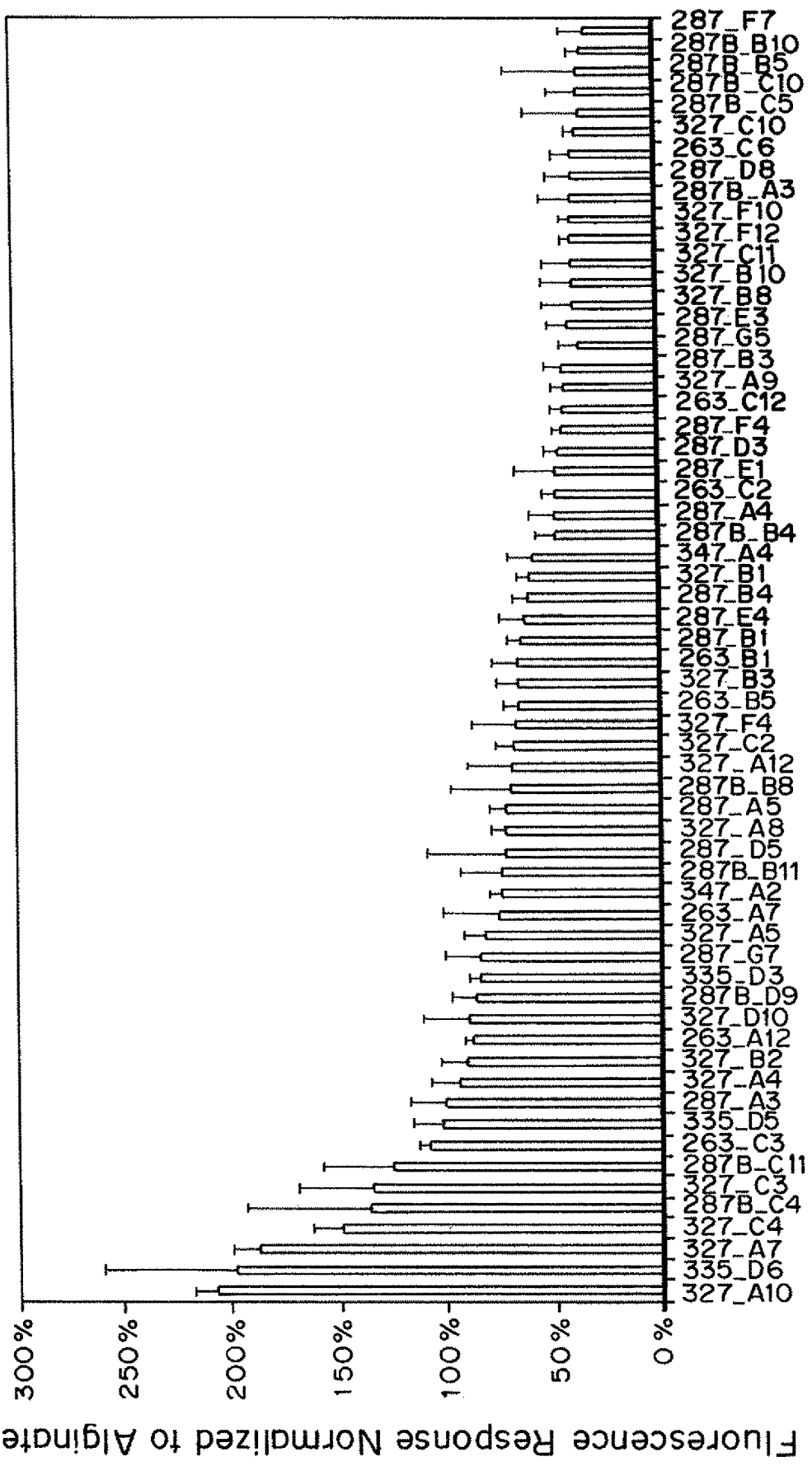

FIG. 4 is a plot obtained using the in vivo method described in Example 5, which quantifies the biocompatibility of selected modified alginates. The fluorescence response obtained for the modified alginates using the in vivo method described in Example 5 was normalized to the fluorescence response measured using unmodified alginate in order to quantify the biocompatibility of the modified alginates in terms of % fluorescence response.

Figure 5:
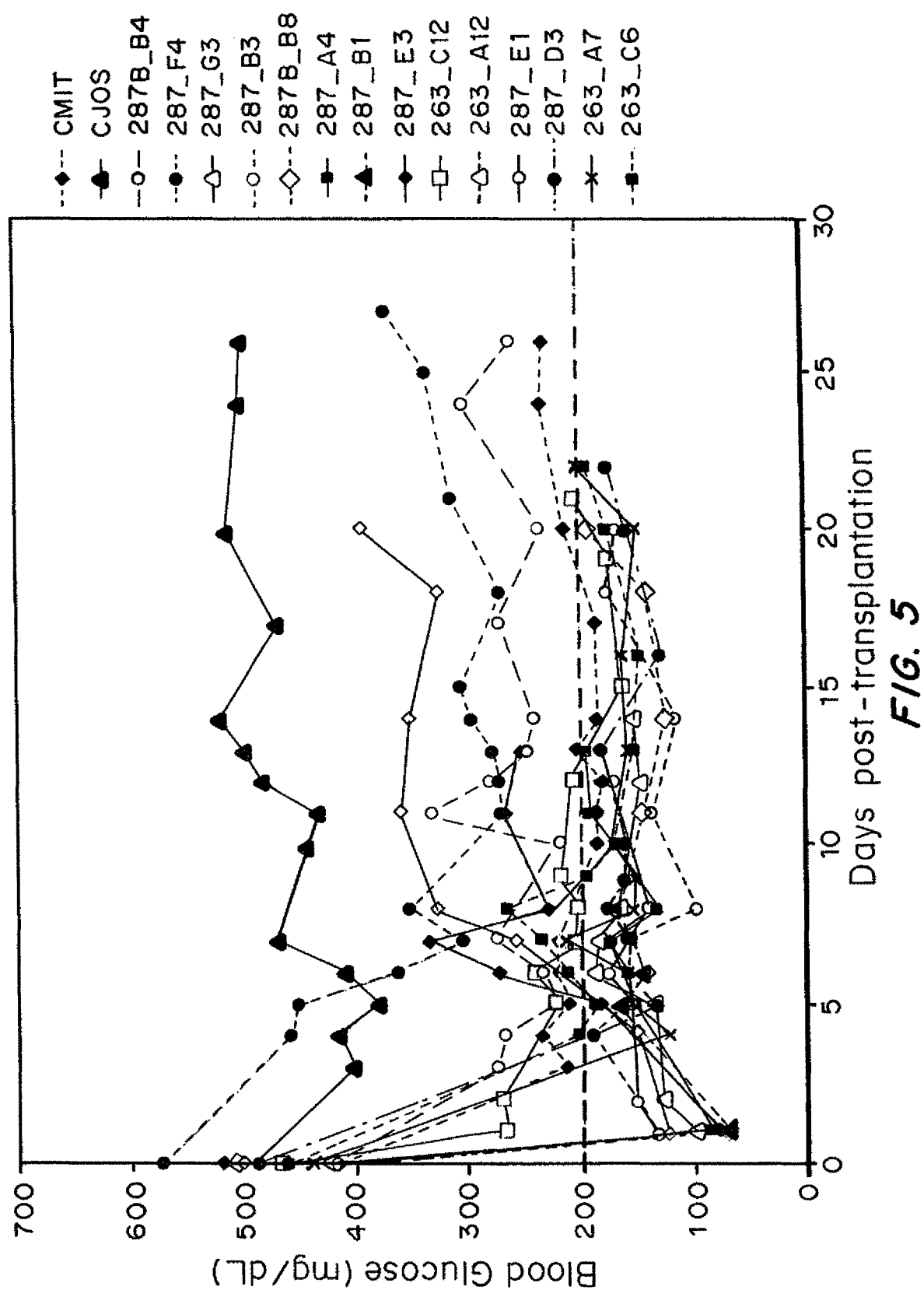

FIG. 5 is a plot detailing the blood glucose level of mice transplanted with rat islets encapsulated in selected modified alginates as well as two different unmodified alginates (CMIT and CJOS). The dashed black line represents normoglycemia in mice.

Figure 6:
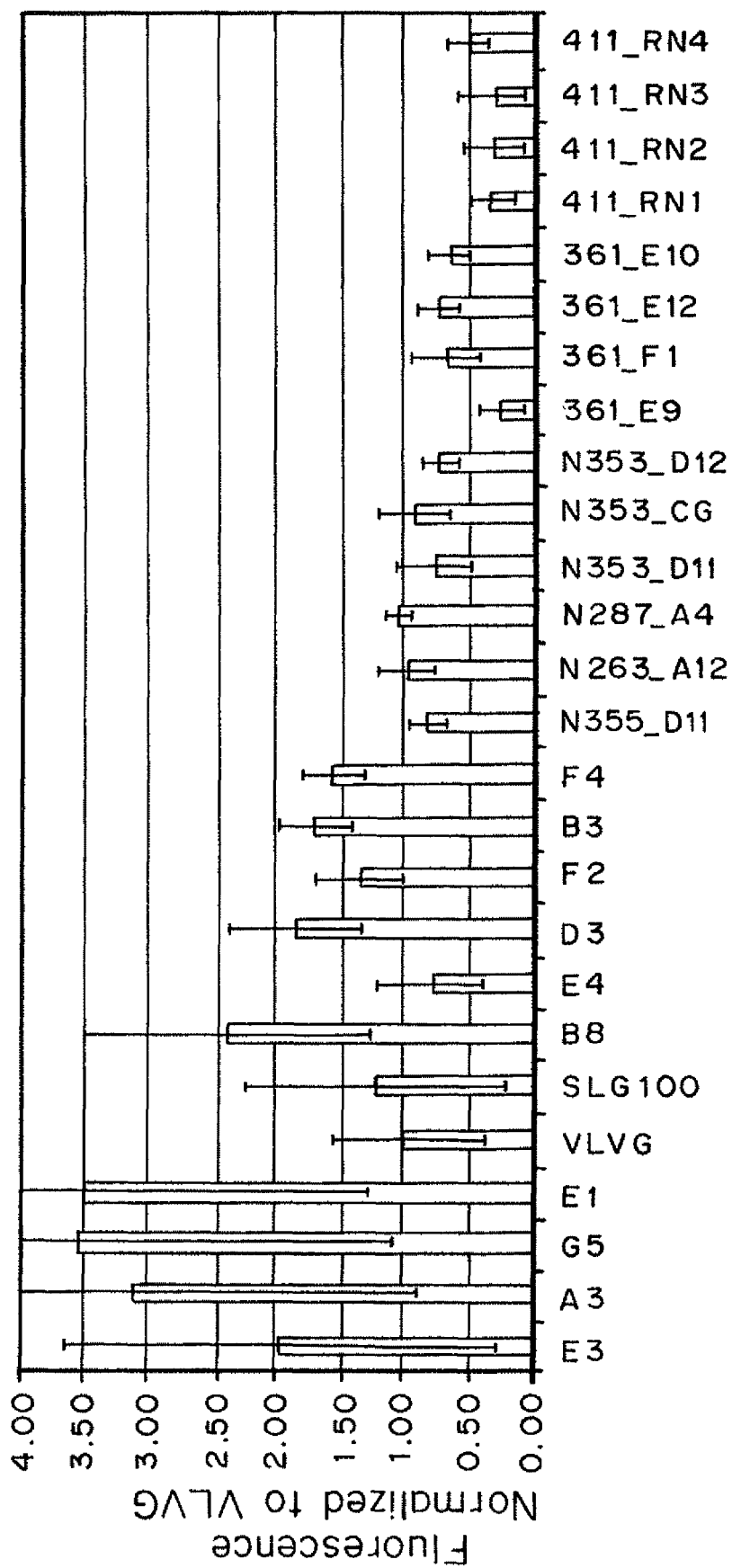

FIG. 6 is a bar graph showing inflammatory response (as measured by fluorescence normalized to VLVG) as a function of modified alginate (combined with unmodified alginate).

DETAILED DESCRIPTION OF THE INVENTION

Alginates are a class of linear polysaccharide copolymers formed from 1-4-glycosidically linked β-D-mannuronate (M) and its C-5 epimer α-L-guluronate (G). Alginates are naturally occurring biopolymers produced by a variety of organisms, including marine brown algae and at least two genera of bacteria (*Pseudomonas* and *Azotobacter*). Typically, commercial alginates are isolated from marine algae, including *Macrocystis pyrifera*, *Ascophyllum nodosum*, and various types of *Laminaria*.

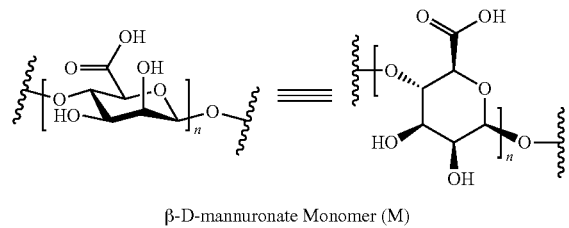

β-D-mannuronate Monomer (M)

-continued

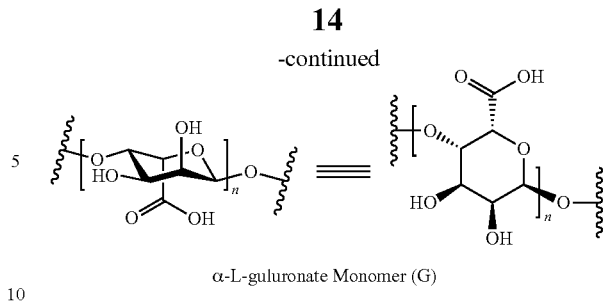

α-L-guluronate Monomer (G)

Three types of primary structure define the polysaccharide backbone of alginates: homopolymeric regions of consecutive guluronate monomers (G-blocks), homopolymeric regions of consecutive mannuronate monomers (M-blocks), and regions containing alternating mannuronate and guluronate monomers (MG-blocks). The monomer blocks possess different conformations in solution, ranging from a flexible extended structure (M-blocks) to a rigid compact structure (G-blocks). In the case of G-blocks, the compact conformation facilitates the chelation of multivalent ions, notably $Ca^{2+}$ ions, such that G-blocks in one alginate chain can be ionically crosslinked with G-blocks in another alginate chain, forming stable gels. As a result, the proportion, length, and distribution of the monomer blocks influence the physiochemical properties of the alginate polymer.

In the case of commercially produced alginates obtained from algae, the molecular weight, primary structure, and overall molar ratio of uronic acid monomers (M/G ratio) in the alginate polymer depends on a number of factors, including the species producing the alginate, the time of year in which the species is collected, and the location and age of the algal body. As a result, alginates possessing a range of physiochemical properties, such as molecular weight and viscosity, are commercially available.

Alginates can be ionically crosslinked at room temperature and neutral pH to form hydrogels. The ability of alginates to form stable gels in physiologically compatible conditions renders alginate gels useful in a number of biomedical applications. For example, alginate gels have be used as a matrix for drug delivery to modulate the pharmacokinetics of therapeutic, diagnostic, and prophylactic agents.

I. Definitions

"Alginate", as used herein, is a collective term used to refer to linear polysaccharides formed from β-D-mannuronate and α-L-guluronate in any M/G ratio, as well as salts and derivatives thereof. The term "alginate", as used herein, encompasses any polymer having the structure shown below, as well as salts thereof.

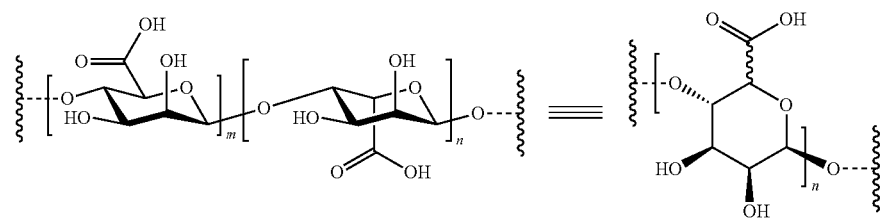

"Biocompatible", as used herein, refers to a material which performs its desired function when introduced into an organism without inducing significant inflammatory response, immunogenicity, or cytotoxicity to native cells, tissues, or organs. Biocompatibility, as used herein, can be quantified using the in vivo biocompatibility assay described herein in Example 5.

"Foreign Body Response", as used herein, refers to the immunological response of biological tissue to the presence of any foreign material in the tissue which can include protein adsorption, macrophages, multinucleated foreign body giant cells, fibroblasts, and angiogenesis.

"Chemically Modified Alginate" or "Modified Alginate", are used herein interchangeably, and refer to alginate polymers which contain one or more covalently modified monomers.

"Covalently Modified Monomer", as used herein, refers to a monomer which is an analog or derivative of a mannuronate and/or guluronate monomer obtained from a mannuronate and/or guluronate monomer via a chemical process.

"Singularly Modified Alginate Polymer", as used herein, refers to modified alginates that contain one or more covalently modified monomers, wherein substantially all of the covalently modified monomers possess the same covalent modification (i.e. the polymer contains one 'type' or species of covalently modified monomer). Singularly modified alginate polymers include, for example, modified alginate polymers wherein substantially all of the monomers in the modified alginate polymer are represented by mannuronate monomers, guluronate monomers, and a covalently modified monomer defined by Formula I. Not all of the monomers are necessarily covalently modified.

For clarity of discussion herein, singularly modified alginates are defined using formulae illustrating the structure of the covalently modified monomers incorporated in the backbone and omitting the mannuronate and guluronate monomers. For example, a singularly modified alginate polymer composed of mannuronate monomers, guluronate monomers, and a covalently modified monomer defined by Formula I, wherein X is NR, $R_1$ is methyl, and R, $Y_1$, and $Y_2$ are hydrogen, is illustrated herein by the structure below.

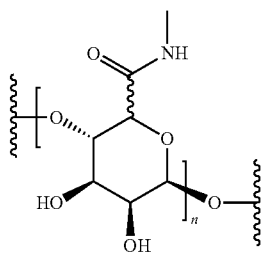

"Multiply Modified Alginate Polymer", as used herein, refers to modified alginates that contain covalently modified monomers, wherein substantially all of the covalently modified monomers do not possess the same covalent modification (i.e. the polymer contains two or more different 'types' or species of covalently modified monomers). Multiply modified alginate polymers include, for example, modified alginate polymers wherein substantially all of the monomers in the modified alginate polymer are represented by mannuronate monomers, guluronate monomers, and two or more different types of covalently modified monomers defined by Formula I. As used in this context, a 'type' or 'species' of covalently modified monomer refers to a covalent monomer defined by Formula I, wherein all possible variable positions are chemically defined. Not all the monomers are covalently modified.

For clarity of discussion herein, modified alginates are defined using formulae illustrating the covalently modified monomers incorporated in the backbone and omitting the mannuronate and guluronate monomers. For example, a multiply modified alginate polymer composed of mannuronate monomers, guluronate monomers, and two different types of covalently modified monomers, wherein the first type of covalently modified monomer is defined by Formula I, wherein X is NR, $R_1$ is methyl, and R, $Y_1$, and $Y_2$ are hydrogen and the second type of covalently modified monomer is defined by Formula I, wherein X is oxygen, $R_1$ is ethyl, and $Y_1$ and $Y_2$ are hydrogen, is illustrated by the structure below.

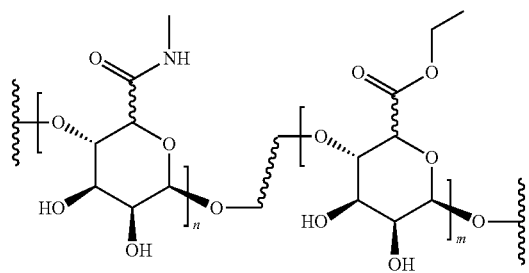

"Analog" and "Derivative" are used herein interchangeably, and refer to a compound having a structure similar to that of a parent compound, but varying from the parent compound by a difference in one or more certain components. Analogs or derivatives differ from the parent compound in one or more atoms, functional groups, or substructures, which are replaced with other atoms, groups, or substructures. An analog or derivative can be imagined to be formed, at least theoretically, from the parent compound via some chemical or physical process. The terms analog and derivative encompass compounds which retain the same basic ring structure as the parent compound, but possess one or more different substituents on the ring(s). For example, analog or derivative of mannuronate or guluronate refers to compounds which retain the core of the monomer, e.g., the pyranose ring, but differ in or more substitutents on the ring.

"Mannuronate" and "Mannuronate Monomer", as used herein, refers to mannuronic acid monomers as well as salts thereof.

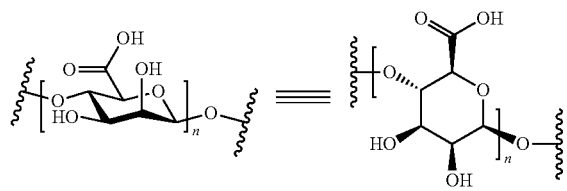

"Guluronate" and "Guluronate Monomer", as used herein, refers to guluronic acid monomers as well as salts thereof.

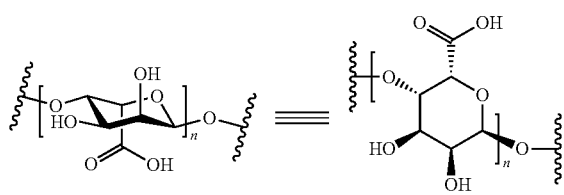

"Substantially", as used herein, specifies an amount of 95% or more, 96% or more, 97% or more, 98% or more, or 99% or more.

"Glass Transition Temperature" ($T_g$), as used herein, refers to the temperature at which a reversible transition is observed in amorphous materials from a hard and relatively brittle state into a molten or rubber-like state. Tg values for alginate polymers can be experimentally determined using differential scanning calorimetry (DSC, heated and cooled at a rate of 10 K/min). In all cases herein, values of $T_g$ are measured using powder polymer samples.

"Click Chemistry", as used herein, refers to chemical reactions used to couple two compounds together which are high yielding, wide in scope, create only byproducts that can be removed without chromatography, are stereospecific, simple to perform, and can be conducted in easily removable or benign solvents. Examples of reactions which fulfill these criteria include the nucleophilic ring opening of epoxides and aziridines, non-aldol type carbonyl reactions, including the formation of hydrazones and heterocycles, additions to carbon-carbon multiple bonds, including Michael Additions, and cycloaddition reactions, such as a 1,3-dipolar cycloaddition reaction (i.e. a Huisgen cycloaddition reaction). See, for example, Moses, J. E. and Moorhouse, A. D. *Chem Soc. Rev.* 2007; 36: 1249-1262; Kolb, H. C. and Sharpless, K. B. *Drug Discovery Today.* 2003; 8(24: 1128-1137; and Kolb, H. C., et al. *Angew. Chem. Int. Ed.* 2001; 40: 2004-2021.

"Polyvalent Cation", as used herein, refers to cations which have a positive charge greater than 1. Examples include, but are not limited to, $Ca^{2+}$, $Ba^{2+}$, and $Sr^{2+}$.

"Substituted", as used herein, refers to all permissible substituents of the compounds or functional groups described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Aryl", as used herein, refers to $C_5$-$C_{10}$-membered aromatic, heterocyclic, fused aromatic, fused heterocyclic, biaromatic, or biheteroeocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

"Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), preferably 20 or fewer, more preferably 10 or fewer, most preferably 6 or fewer. If the alkyl is unsaturated, the alkyl chain generally has from 2-30 carbons in the chain, preferably from 2-20 carbons in the chain, more preferably from 2-10 carbons in the chain. Likewise, preferred cycloalkyls have from 3-20 carbon atoms in their ring structure, preferably from 3-10 carbons atoms in their ring structure, most preferably 5, 6 or 7 carbons in the ring structure.

The terms "alkenyl" and "alkynyl" refer to unsaturated aliphatic groups analogous in length and possible substitution to the alkyls described above, but that contain at least one double or triple bond respectively.

"Alkyl" includes one or more substitutions at one or more carbon atoms of the hydrocarbon radical as well as heteroalkyls. Suitable substituents include, but are not limited to, halogens, such as fluorine, chlorine, bromine, or iodine; hydroxyl; —$NR_1R_2$, wherein $R_1$ and $R_2$ are independently hydrogen, alkyl, or aryl, and wherein the nitrogen atom is optionally quaternized; —SR, wherein R is hydrogen, alkyl, or aryl; —CN; —$NO_2$; —COOH; carboxylate; —COR, —COOR, or —$CONR_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, —$CF_3$; —CN; —$NCOCH_2CH_2$; —NCOCOCHCH; —NCS; and combinations thereof.

"Amino" and "Amine", as used herein, are art-recognized and refer to both substituted and unsubstituted amines, e.g., a moiety that can be represented by the general formula:

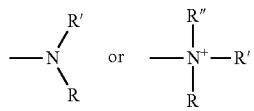

wherein, R, R', and R" each independently represent a hydrogen, substituted or unsubstituted alkyl, substituted or unsubstituted alkenyl, substituted or unsubstituted alkynyl, substituted or unsubstituted carbonyl, —$(CH_2)_m$—R''', or R and R' taken together with the N atom to which they are attached complete a heterocycle having from 3 to 14 atoms in the ring structure; R''' represents a hydroxy group, substituted or unsubstituted carbonyl group, an aryl, a cycloalkyl ring, a cycloalkenyl ring, a heterocycle, or a polycycle; and m is zero or an integer ranging from 1 to 8. In preferred embodiments, only one of R and R' can be a carbonyl, e.g., R and R' together with the nitrogen do not form an imide. In preferred embodiments, R and R' (and optionally R") each independently represent a hydrogen atom, substituted or unsubstituted alkyl, a substituted or unsubstituted alkenyl, or —$(CH_2)_m$—R'''. Thus, the term 'alkylamine' as used herein refers to an amine group, as defined above, having a substituted or unsubstituted alkyl attached thereto (i.e. at least one of R, R', or R" is an alkyl group).

"Carbonyl", as used herein, is art-recognized and includes such moieties as can be represented by the general formula:

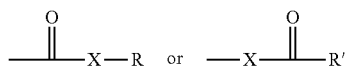

wherein X is a bond, or represents an oxygen or a sulfur, and R represents a hydrogen, a substituted or unsubstituted alkyl, substituted or unsubstituted alkenyl, substituted or unsubstituted alkynyl, —$(CH_2)_m$—R", or a pharmaceutical acceptable salt, R' represents a hydrogen, substituted or unsubstituted alkyl, substituted or unsubstituted alkenyl, substituted or unsubstituted alkynyl, or —$(CH_2)_m$—R"; R" represents a hydroxy group, substituted or unsubstituted carbonyl group, an aryl, a cycloalkyl ring, a cycloalkenyl ring, a heterocycle, or a polycycle; and m is zero or an integer ranging from 1 to 8. Where X is oxygen and R is defines as above, the moiety is also referred to as a carboxyl group. When X is oxygen and R is hydrogen, the formula represents a 'carboxylic acid'. Where X is oxygen and R' is hydrogen, the formula represents a 'formate'. In general, where the oxygen atom of the above formula is replaced by a sulfur, the formula represents a 'thiocarbonyl' group. Where X is sulfur and R or R' is not hydrogen, the formula represents a 'thioester'. Where X is sulfur and R is hydrogen, the formula represents a 'thiocarboxylic acid'. Where X is sulfur and R' is hydrogen, the formula represents a 'thioformate'. Where X is a bond and R is not hydrogen, the above formula represents a 'ketone'. Where X is a bond and R is hydrogen, the above formula represents an 'aldehyde'.

"Heteroalkyl", as used herein, refers to straight or branched chain, or cyclic carbon-containing radicals, or combinations thereof, containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized.

Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl.

"Alkoxy", "alkylamino", and "alkylthio" are used herein in their conventional sense, and refer to those alkyl groups attached to the remainder of the molecule via an oxygen atom, an amino group, or a sulfur atom, respectively.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocycle or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, (uranyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents as defined above for alkyl and aryl.

le;.5q"Halogen", as used herein, refers to fluorine, chlorine, bromine, or iodine.

II. Modified Alginates le;.5qDescribed herein are alginate polymers that have been chemically modified to alter their biocompatibility and physical properties, as well as methods of making thereof.

A. Structure of Modified Alginate Polymers

Modified alginates contain one or more covalently modified monomers defined by Formula I

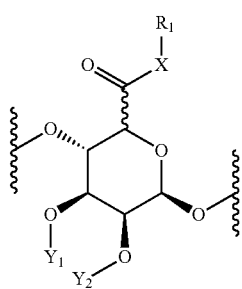

Formula I wherein,

X is oxygen, sulfur, or NR;

$R_1$ is hydrogen, or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative $R_1$ groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group;

$Y_1$ and $Y_2$ independently are hydrogen or —PO(OR)$_2$; or $Y_2$ is absent, and $Y_2$, together with the two oxygen atoms to which $Y_1$ and $Y_2$ are attached form a cyclic structure as shown below

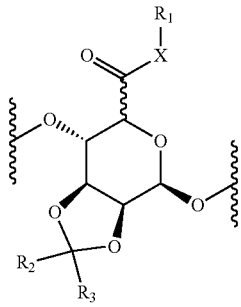

wherein n is an integer between 1 and 4; and $R_2$ and $R_3$ are, independently, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group; or $R_2$ and $R_3$, together with the carbon atom to which they are attached, form a 3- to 8-membered unsubstituted or substituted carbocyclic or heterocyclic ring; and R is, independently for each occurrence, hydrogen or an organic grouping containing any number of carbon atoms, preferably 1-30 carbon atoms, more preferably 1-20 carbon atoms, more preferably 1-14 carbon atoms, and optionally including one or more heteroatoms such as oxygen, sulfur, or nitrogen grouping in linear, branched, or cyclic structural formats, representative R groupings being alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, carbonyl, substituted carbonyl, carboxyl, substituted carboxyl, amino, substituted amino, amido, substituted amido, polyaryl, substituted polyaryl, $C_3$-$C_{20}$ cyclic, substituted $C_3$-$C_{20}$ cyclic, heterocyclic, substituted heterocyclic, aminoacid, poly(ethylene glycol), peptide, or polypeptide group.

In some embodiments, the modified alginate polymer is a singularly modified alginate polymer. In specific embodiments, the singularly modified alginate polymer contains one or more covalently modified monomers defined by Formula I, wherein $R_1$ includes an azide group, an alkyne group, or a 1,2,3-triazole ring. In certain embodiments, the singularly modified alginate polymer contains one or more covalently modified monomers defined by Formula I, wherein X is not oxygen and $R_1$ is not an unsubstituted $C_1$-$C_{18}$ alkyl group, poly(ethylene glycol) chain, or cholesteryl moiety. In certain additional embodiments, the singularly modified alginate polymer contains one or more covalently modified monomers defined by Formula I, wherein X is not NR and $R_1$ is not a substituted or unsubstituted $C_1$-$C_6$ alkyl group, or a poly(ethylene glycol) chain.

In alternative embodiments, the modified alginate polymer is a multiply modified alginate polymer. In preferred embodiments, the multiply modified alginate polymer possesses a polysaccharide backbone containing mannuronate monomers, guluronate monomers, a first species or type of covalently modified monomer defined by Formula I, and a second species or type of covalently modified monomer defined by Formula I. In other embodiments, the multiply modified alginate polymer possesses a polysaccharide backbone containing mannuronate monomers, guluronate monomers, and three or more different types of covalently modified monomers defined by Formula I.

In some embodiments, the multiply modified alginate polymer contains two different species of covalently modified monomers defined by Formula I, wherein in both species of monomer, X is NR. In other embodiments, the multiply modified alginate polymer contains two different species of covalently modified monomers defined by Formula I, wherein in both species of monomer, X is oxygen. In further embodiments, the multiply modified alginate polymer contains two different species of covalently modified monomers defined by Formula I, wherein in one species of monomer X is oxygen, and in the second species of monomer, X is NR.

In some embodiments, the multiply modified alginate polymer contains two different species of covalently modified monomers defined by Formula I, wherein in at least one species of monomer, $R_1$ includes one or more cyclic moieties. In preferred embodiments, the multiply modified alginate polymer contains two different species of covalently modified monomers defined by Formula I, wherein in at least one species of monomer, $R_1$ includes a phenyl ring, furan ring, oxolane ring, dioxolane ring, or a 1,2,3-triazole ring.

In certain embodiments, the multiply modified alginate polymer contains two different species of covalently modified monomers defined by Formula I, wherein in at least one species of monomer, $R_1$ includes one or more halogen moieties, an azide group, or an alkyne.

In preferred embodiments, the multiply modified alginate polymer is one of the multiply modified alginate polymers shown below.

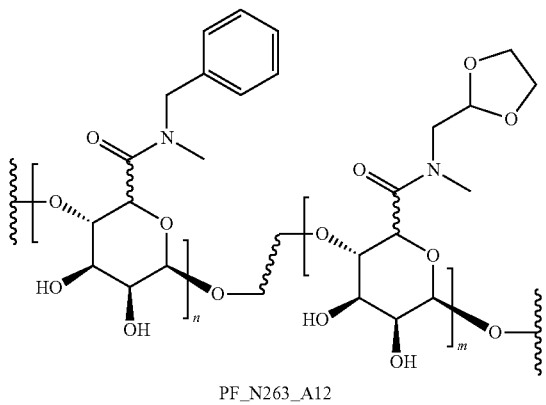

PF_N263_A12

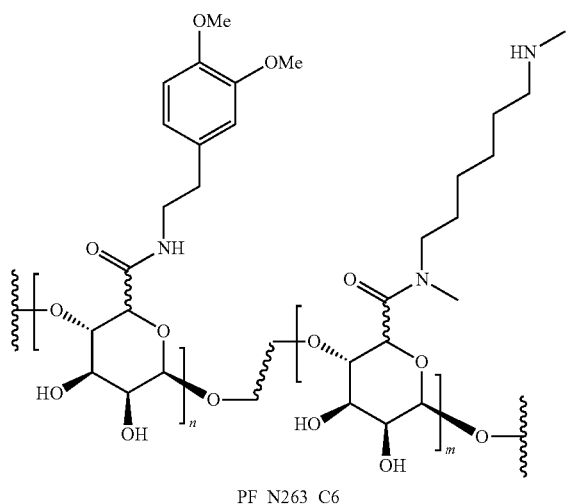

PF_N263_C6

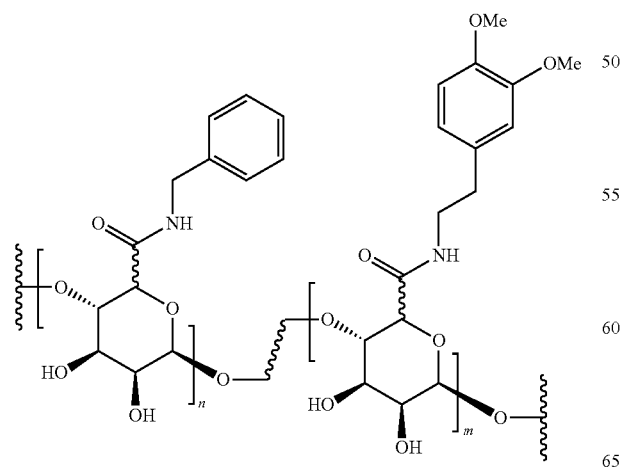

PF_N263_A7

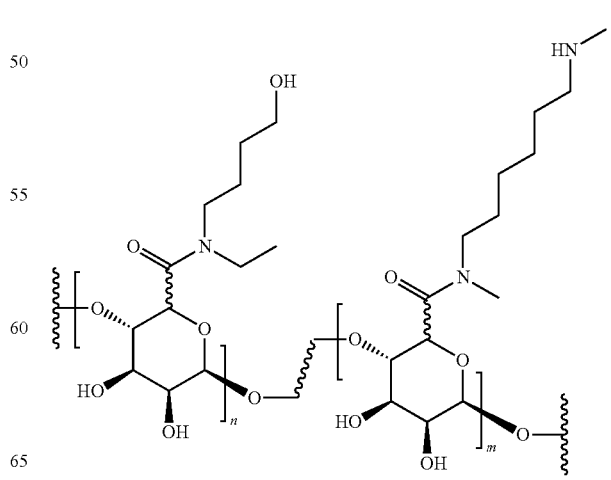

PF_N263_C12

25
-continued
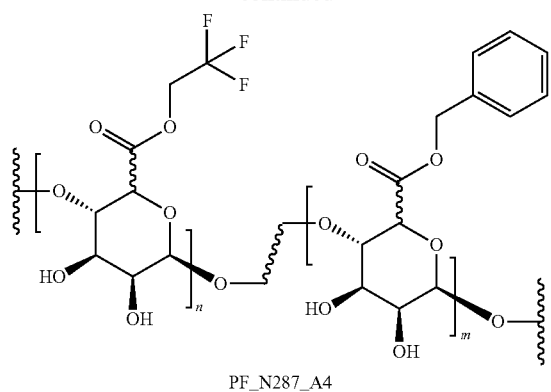
PF_N287_A4
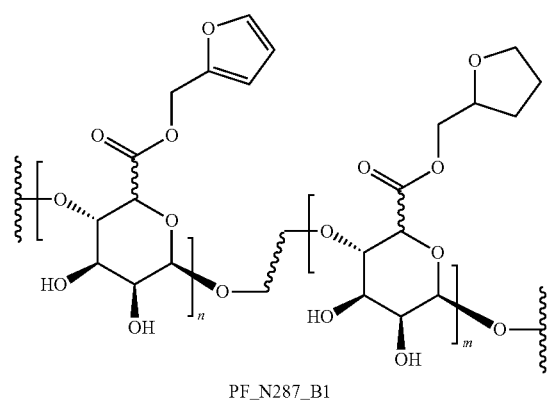
PF_N287_B1
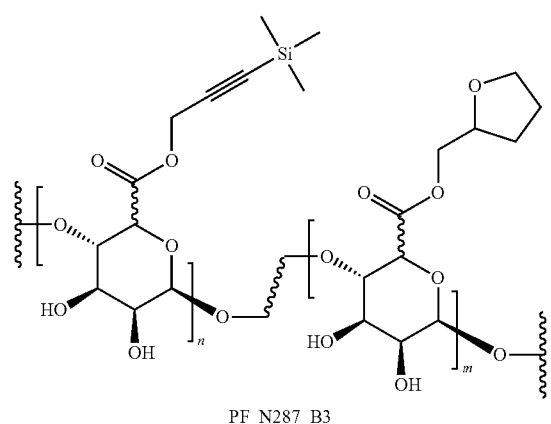
PF_N287_B3
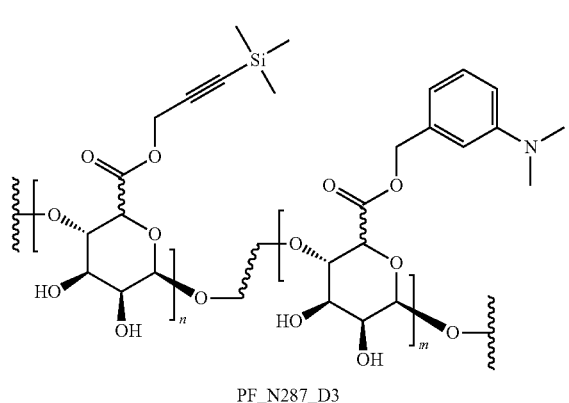
PF_N287_D3
26
-continued
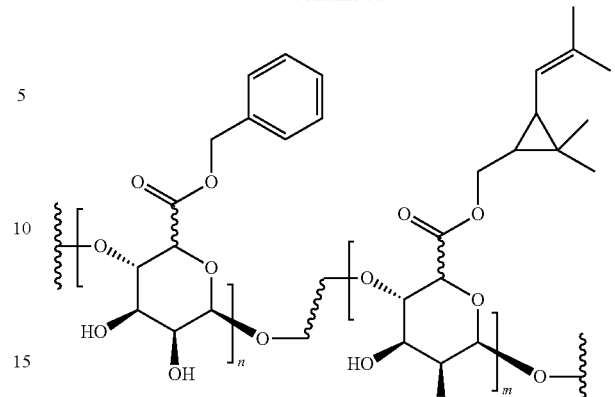
PF_N263_E1
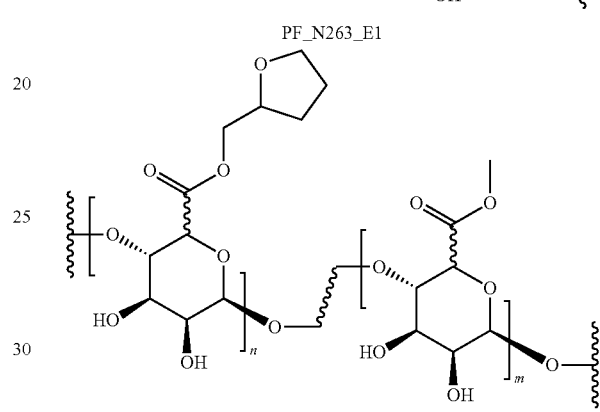
PF_N287_G5
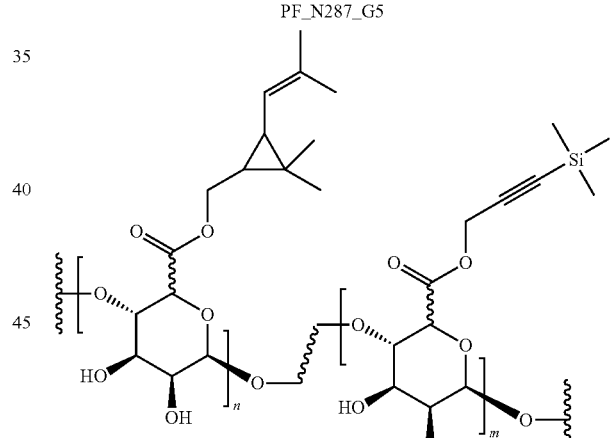
PF_N287_F4
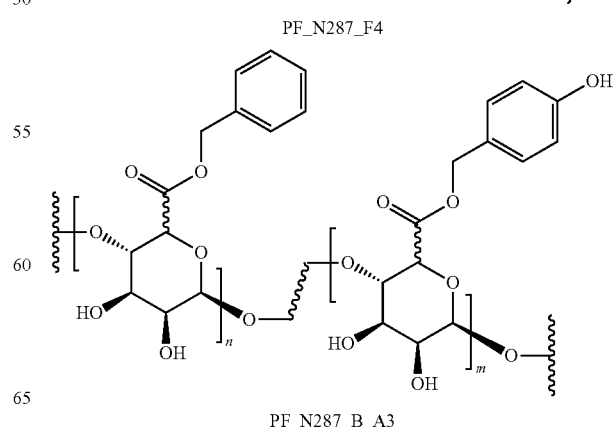
PF_N287_B_A3

27
-continued
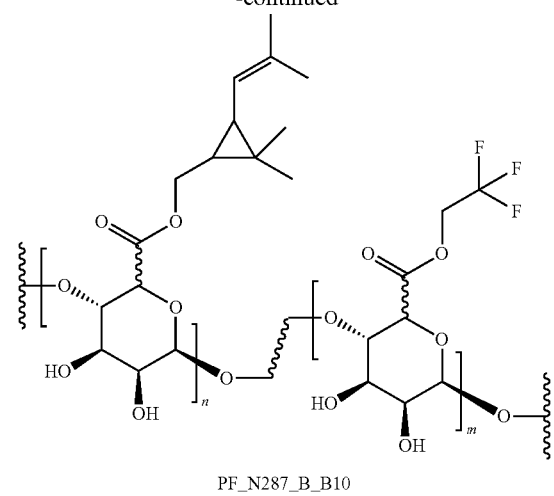
PF_N287_B_B10
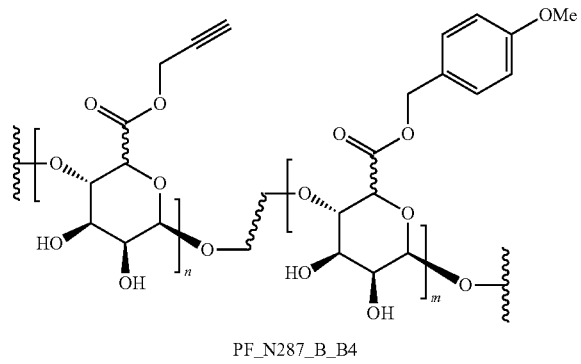
PF_N287_B_B4
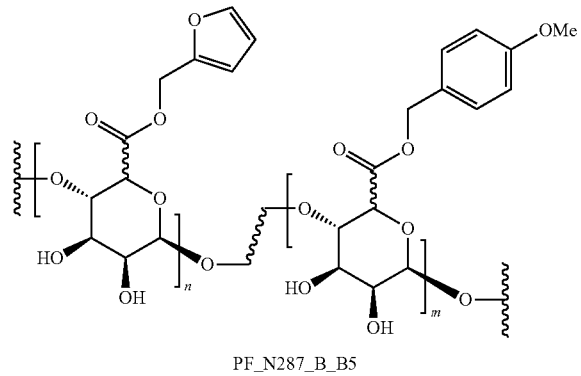
PF_N287_B_B5
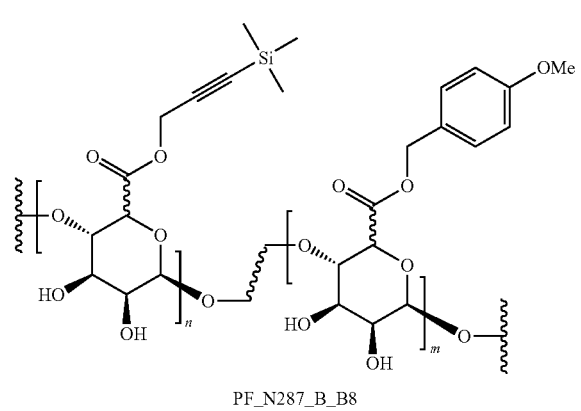
PF_N287_B_B8
28
-continued
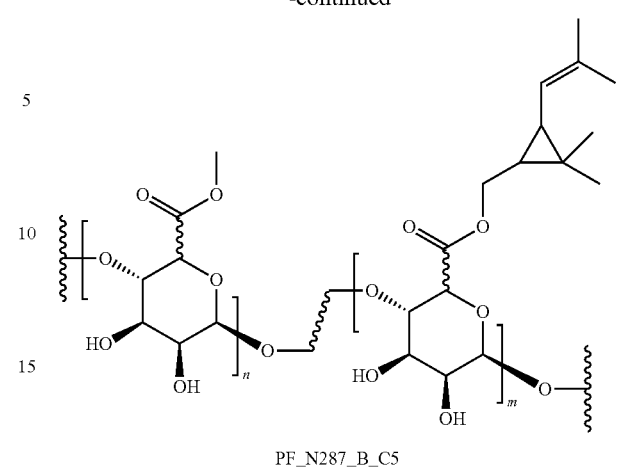
PF_N287_B_C5
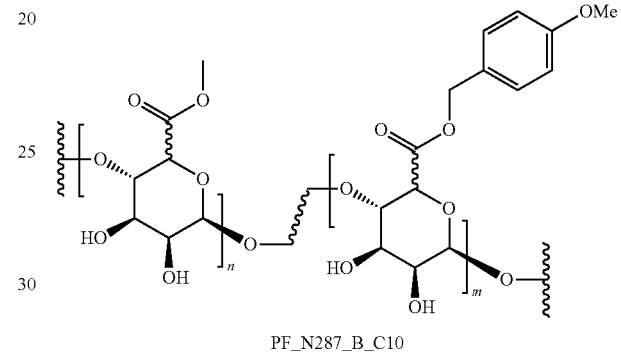
PF_N287_B_C10
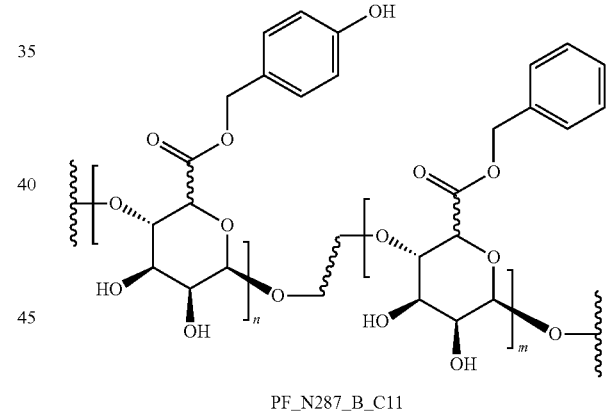
PF_N287_B_C11
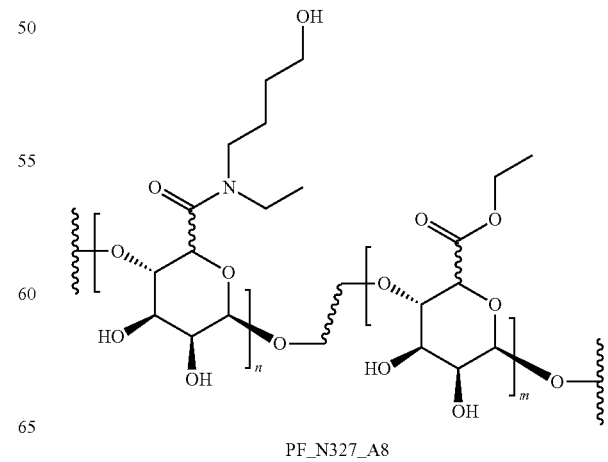
PF_N327_A8

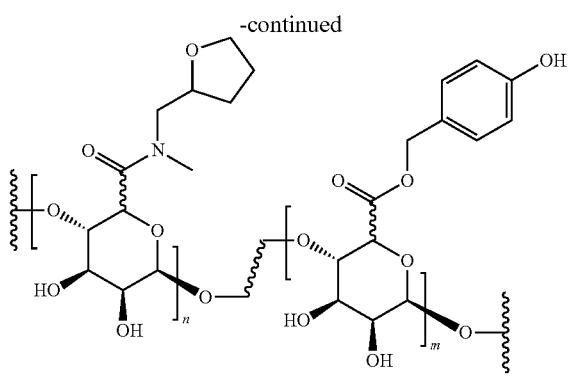

PF_N327_B8

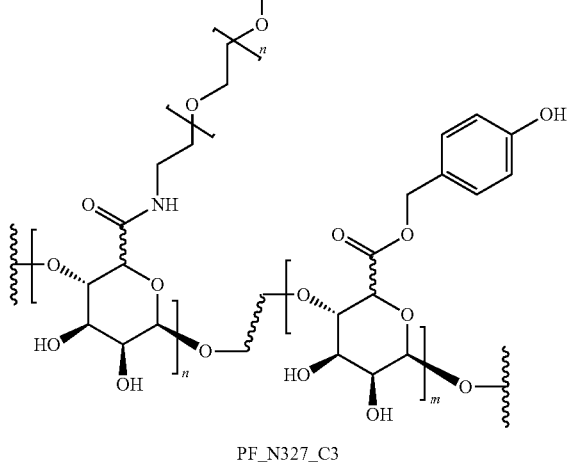

PF_N327_B10

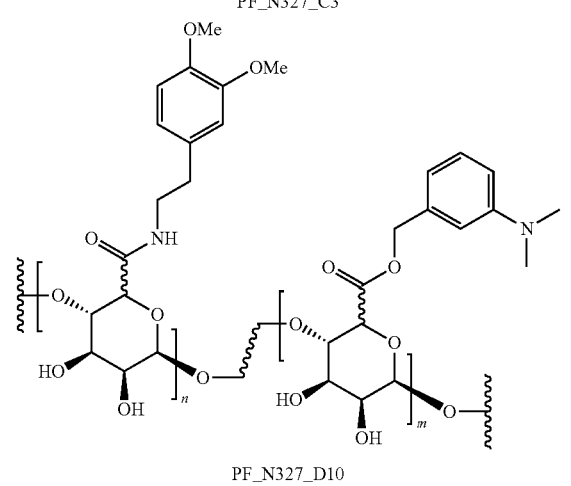

PF_N327_C3

PF_N327_D10

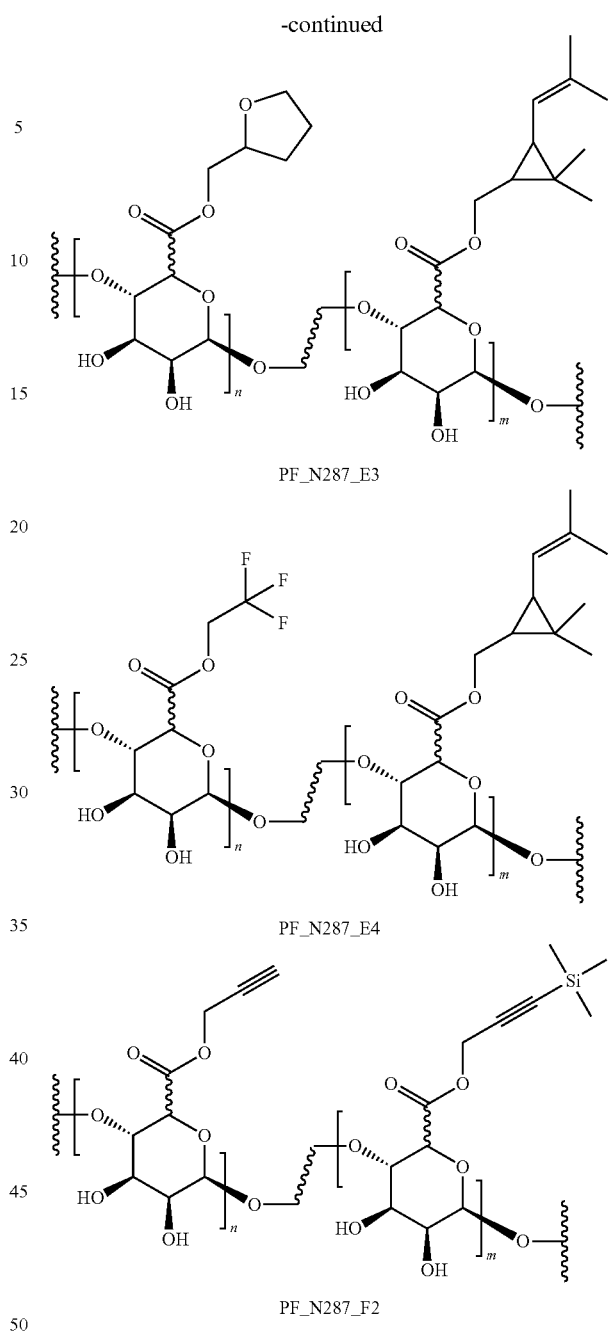

PF_N287_E3

PF_N287_E4

PF_N287_F2

Modified alginate polymers can be of any desired molecular weight. The weight average molecular weight of the alginates is preferably between 1,000 and 1,000,000 Daltons, more preferably between 10,000 and 500,000 Daltons as determined by gel permeation chromatography.

Modified alginate polymers can contain any ratio of mannuronate monomers, guluronate monomers, and covalently modified monomers. In some embodiments, greater than 2.5%, 5%, 7.5%, 10%, 12%, 14%, 15%, 16%, 18%, 20%, 22%, 24%, 25%, 26%, 28%, 30%, 32.5%, 35%, 37.5%, 40%, 45%, 50%, 55%, or 60% of the monomers in the modified alginate polymer are covalently modified monomers. Preferably greater than 20%, more preferably greater than 25%, and most preferably greater than 30% of the monomers in the modified alginate polymer are covalently modified monomers.

Modified alginate polymers can be produced incorporating covalently modified monomers possessing a range of different hydrogen bonding potentials, hydrophobicities/hydrophilicities, and charge states. The inclusion of covalently modified monomers into an alginate polymer alters the physiochemical properties of alginate polymer. Accordingly, the physiochemical properties of alginates can be tuned for desired applications by the selective incorporation of covalently modified monomers.

For example, the glass transition temperature ($T_g$), can be varied by the incorporation of covalently modified monomers. In some embodiments, the modified alginate polymer powder possess a $T_g$, as measured by differential scanning calorimetry (DSC), of greater than 50° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 160° C., 175° C., 190° C., or 200° C.

The hydrophobicity/hydrophilicity of alginates can be varied by the incorporation of hydrophobic and/or hydrophilic covalently modified monomers. In preferred embodiments, the modified alginate polymer contains one or more hydrophobic covalently modified monomers. The relative hydrophobicity/hydrophilicity of modified alginates can be quantitatively assessed by measuring the contact angle of a water droplet on a film of the modified alginate polymer using a goniometer. In some embodiments, the modified alginate has a contact angle of less than 90° (i.e. it is hydrophilic). In preferred embodiments, the modified alginate has a contact angle of more than 90° (i.e. it is hydrophobic). In some embodiments, the modified alginate has a contact angle of more than 95°, 100°, 105°, 110°, 115°, or 120°.

In embodiments used for cell encapsulation, the modified alginate polymer can be ionically crosslinked by a polyvalent cation such as $Ca^{2+}$, $Sr^{2+}$, or $Ba^{2+}$ to form hydrogels. The ability of modified alginates to form stable hydrogels in physiological conditions can be quantified using the hydrogel formation assay described in Example 2.

In some embodiments, the modified alginate polymer forms hydrogels such that the fluorescence intensity measured using the high throughput hydrogel formation assay described herein is greater than 10,000, 15,000, 20,000, 25,000, 30,000, 35,000, 40,000, 45,000, 50,000, or 55,000. In preferred embodiments, the modified alginate polymer forms hydrogels such that the fluorescence intensity measured using the high throughput hydrogel formation assay described herein is greater than 15,000. In preferred embodiments, the modified alginate polymer forms hydrogels such that the fluorescence intensity measured using the high throughput hydrogel formation assay described herein is between 15,000 and 55,000, preferably between 20,000 and 55,000, more preferably between 25,000 and 55,000.

In embodiments used for cell encapsulation, the modified alginate polymer forms a hydrogel with sufficient porosity to permit nutrients, waste, and the hormones and/or proteins secreted from encapsulated cells to diffuse freely into and out of the microcapsules, while simultaneously preventing the incursion of immune cells into the gel matrix. The porosity and surface area of modified alginate hydrogels can be measured using BET analysis. Prior to BET analysis, solvent and volatile impurities are removed by prolonged heating of the modified alginate gel under vacuum. Subsequently, the hydrogel samples are cooled under vacuum, for example by liquid nitrogen, and analyzed by measuring the volume of gas (typically $N_2$, Kr, $CO_2$, or Ar gas) adsorbed to the hydrogel at specific pressures. Analysis of the physisorption of the gas at variable pressures is used to characterize the total surface area and porosity of gels formed by the modified alginate polymers. The preferred method of determining hydrogel porosity is BET analysis.

In preferred embodiments, the modified alginate forms a hydrogel with sufficient porosity to permit nutrients, waste, and the hormones and/or proteins secreted from encapsulated cells to diffuse freely into and out of the microcapsules, while simultaneously preventing the incursion of immune cells into the gel matrix. In some embodiments, the porosity of the hydrogel formed by the modified alginate polymer is increased by 5%, 10%, 15%, or 20% relative to the porosity of a hydrogel formed from the unmodified alginate polymer. In alternative embodiments, the porosity of the hydrogel formed by the modified alginate polymer is decreased by 5%, 10%, 15%, or 20% relative to the porosity of a hydrogel formed from the unmodified alginate polymer.

In preferred embodiments used for cell encapsulation, the modified alginate is biocompatible. The biocompatibility of modified alginates can be quantitatively determined using the fluorescence-based in vivo biocompatibility assay described in Example 5. In this assay, cathepsin activity was measured using an in vivo fluorescence assay to quantify the foreign body response to the modified alginate.

In some embodiments, the modified alginate polymer is biocompatible such that the fluorescence response normalized to unmodified alginate measured using the in viva biocompatibility assay described herein is less than 100%, 95%, 90%, 85%, 80%, 75%, 70%, 65%, 60%, 55%, 50%, 45%, or 40%. In preferred embodiments, the modified alginate polymer induces a lower foreign body response than unmodified alginate. This is indicated by fluorescence response normalized to unmodified alginate of less than 100%. In some embodiments, the modified alginate polymer is biocompatible such that the fluorescence response normalized to unmodified alginate measured using the in vivo biocompatibility assay described herein is less than 75%, more preferably less than 65%, and most preferably less than 50%.

B. Particle Morphology

The growing recognition of the parameters driving fibrosis in vivo has been applied to the analysis of the performance of modified alginates. Intraperitoneal (IP) implantation of modified alginate capsules revealed that modified alginates may result in abnormally shaped capsules when crosslinked using conditions defined for unmodified alginates. These abnormally shaped capsules can complicate implementation and interpretation of modified alginate capsules implanted IP. In an effort to improve the capsule morphology, formulation methods for use with modified alginate microparticles were developed where modified alginates were blended with a small amount of high molecular weight alginate. Particles prepared from this mixture yielded particles with improved morphology and stability.

The unmodified alginate typically has a weight average molecular weight of about 50,000 Daltons to about 500,000 Daltons; however, unmodified alginates having molecular weights can also be used. In some embodiments, the weight average molecular weight is from about 50,000 to about 250,000 Daltons, more preferably from about 50,000 to about 150,000 Daltons. In some embodiments, the weight average molecular weight is about 100,000 Daltons.

In other embodiments, one or more additional hydrogel-forming polymers are used in combination with unmodified alginate or in place of unmodified alginate. Such polymers are known in the art. Examples include, but are not limited to, PEG, chitosan, dextran, hyaluronic acid, silk, fibrin, polyvinyl alcohol) and poly(hydroxyl ethyl methacrylate).

For example, particles prepared from modified alginate 263_A12 microparticles formulated with barium and mannitol were compared to particles prepared from 263_A12 blended with a small amount of unmodified SLG100 alginate (16% by weight). The particles prepared from a mixture of modified alginate and unmodified alginate produced more homogenous microparticle populations in terms of shape and size as evaluated by scanning electron microscopy (SEM). Quantitative fluorescence analysis with prosense at several time points with modified alginates blended with SLG100 showed that several reformulated modified alginates display less inflammatory response at day 7 compared to the control alginate. Initial experiments with large capsules (1.5 mm diameter) were comparably clean capsules after 2 weeks in the IP space of immunocompetent C57BL6 mice.

C. Preparation of Modified Alginate Polymers

Modified alginates can be prepared through covalent modification of any available alginate polymer. Covalently modified monomers can be introduced into alginate polymers using a variety of synthetic procedures known in the art. In some embodiments, mannuronate and guluronate monomers are covalently modified via esterification and/or amidation of their carboxylic acid moiety. In alternative embodiments, mannuronate and guluronate monomers are covalently modified via phosphorylation or acetal formation. Stoichiometric variation of the reactants during covalent modification can be used to vary the amount of covalently modified monomer incorporated into the modified alginate.

In addition to the reactions discussed below, alternative synthetic methodologies for the covalent modification of mannuronate and guluronate monomers are known in the art. (see, for example, March, "Advanced Organic Chemistry," 5th Edition, 2001, Wiley-Interscience Publication, New York).

1. Modification Via the Carboxylate Moiety of the Mannuronate and Guluronate Monomers Mannuronate and guluronate monomers contain a carboxylic acid moiety which can serve as a point of covalent modification. In preferred embodiments, the carboxylic acid moiety present on one or more mannuronate and/or guluronate residues (1) are reacted as shown in Scheme 1.

Scheme 1.

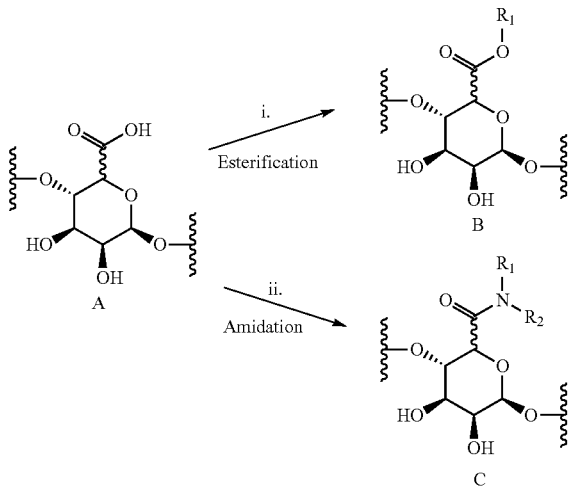

Representative Reaction Conditions: i. HO—R$_1$, 2-Chloro-4,6-dimethoxy-1,3,5-triazine (CDMT), N-methyl morpholine (NMM); ii. HNR$_1$R$_2$, CDMT, NMM.

Mannuronate and guluronate residues (A) can be readily esterified by a variety of methods known in the art, forming covalently modified monomer B. For example, using a Steglich Esterification, mannuronate and guluronate residues (A) can be esterified by reaction with any suitable alcohol (HO—R$_1$) in the presence of a carbodiimide (for example, N,N'-dicyclohexylcarbodiimide (DCC), N,N'-diisopropylcarbodiimide (DIC), or 1-ethyl-3-(3-dimethylaminopropyl) carbodiimide (EDC)) and dimethylaminopyridine (DMAP). In a preferred method, mannuronate and guluronate residues (A) were esterified by reaction with a large molar excess of an alcohol (HO—R$_1$) in the presence of 2-Chloro-4,6-dimethoxy-1,3,5-triazine (CDMT) and N-methyl morpholine (NMM). See, for example, Garrett, C. E. et al. *Tetrahedron Lett*. 2002; 43(23): 4161-4164. Preferred alcohols for use as reagents in esterification include those shown below.

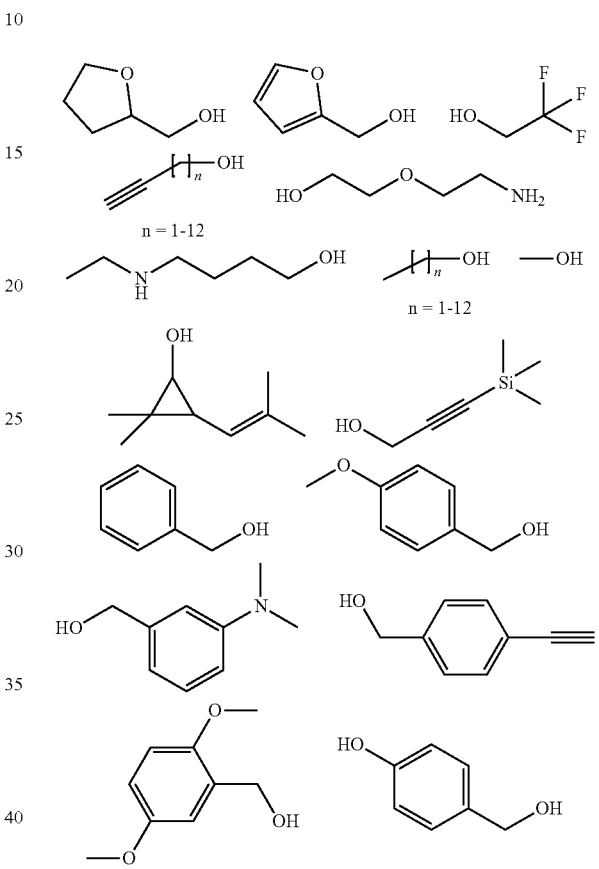

Mannuronate and guluronate residues (A) can also be covalently modified via amidation, forming modified monomer C. For example, mannuronate and guluronate residues (A) can amidated by reaction with any suitable amine (R$_1$—NH$_2$) in the presence of a carbodiimide and DMAP. In a preferred method, mannuronate and guluronate residues (A) were amidated by reaction with a stoichiometric amount of a suitable amine (R$_1$—NH$_2$) in the presence of CDMT and NMM. Preferred amines for use as reagents in amidation reactions include those shown below.

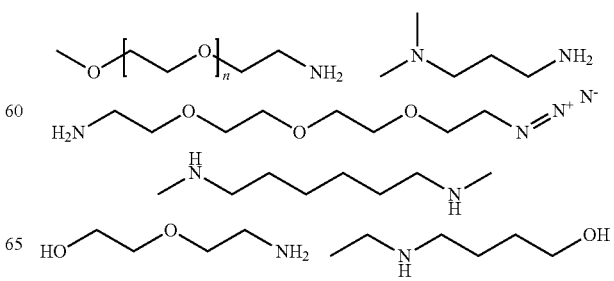

-continued

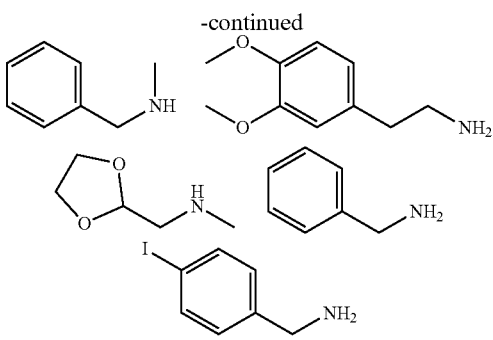

2. Modification of Mannuronate and Guluronate Monomers Via Click Chemistry

In some embodiments, mannuronate and guluronate monomers are covalently modified to introduce a functional group which can be further reacted via click chemistry.

In preferred embodiments, amidation and/or esterification is used to introduce a functional group which can further reacted using a 1,3-dipolar cycloaddition reaction (i.e. a Huisgen cycloaddition reaction). In a 1,3-dipolar cycloaddition reaction, a first molecule containing an azide moiety is reacted with a second molecule containing a terminal or internal alkyne. As shown below, the azide and the alkyne groups undergo an intramolecular 1,3-dipolar cycloaddition reaction, coupling the two molecules together and forming a 1,2,3-triazole ring.

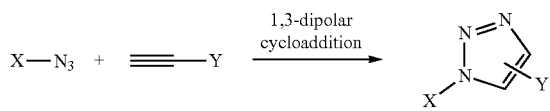

The regiochemistry of 1,3-dipolar cycloadditions reaction can be controlled by addition of a copper(I) catalyst (formed in situ by the reduction of $CuSO_4$ with sodium ascorbate) or a ruthenium catalyst (such as $Cp*RuCl(PPh_3)_2$, $Cp*Ru(COD)$, or $Cp*[RuCl_4]$). For example, using a copper catalyst, azides and terminal alkynes can be reacted to exclusively afford the 1,4-regioisomers of 1,2,3-triazoles. Similarly, in the presence of a suitable ruthenium catalyst, azides can be reacted with internal or terminal alkynes to form exclusively the 1,5-regioisomers of 1,2,3-triazoles.

In some embodiments, amidation and/or esterification is used to form a covalently modified monomer containing an alkyne moiety. In these embodiments, the alkyne moiety present on the covalently modified monomer can be further reacted with a second molecule containing an azide functional group. Upon reaction, the azide and the alkyne groups undergo an intramolecular 1,3-dipolar cycloaddition reaction forming a 1,2,3-triazole ring, coupling the second molecule to the covalently modified monomer.

In alternative embodiments, amidation and/or esterification is used to form a covalently modified monomer containing an azide moiety. In these embodiments, the azide moiety present on the covalently modified monomer can be further reacted with a second molecule containing a terminal or internal alkyne. Upon reaction, the azide and the alkyne groups undergo an intramolecular 1,3-dipolar cycloaddition reaction forming a 1,2,3-triazole ring, coupling the second molecule to the covalently modified monomer.

In preferred embodiments, amidation is used to form a covalently modified monomer containing an azide moiety. Subsequently, the azide moiety present on the covalently modified monomer is reacted with a second molecule containing a terminal or internal alkyne, forming a 1,2,3-triazole ring and coupling the second molecule to the covalently modified monomer.

As shown in Scheme 2, different strategies can be employed to prepare covalently modified monomers containing an azide moiety. For example, mannuronate and guluronate residues (A) can amidated by reaction with an amine substituted with an azide moiety (for example, 11-Azido-3,6,9-trioxaundecan-1-amine) in the presence of a carbodiimide and DMAP, forming azide-functionalized modified monomer F in a single synthetic step. Alternatively, mannuronate and guluronate residues (A) can amidated by reaction with an amine substituted with any moiety which can be readily transformed into an azide. For example, mannuronate and guluronate residues can be amidated by reaction with 4-iodobenzylamine in the presence of a carbodiimide and DMAP, forming iodo-functionalized monomer D. The iodine moiety can then be readily converted to the azide, for example by treatment with sodium azide.

Subsequently, the azide-functionalized monomers can be reacted with a molecule containing an alkyne functionality. For example, azide-functionalized monomers F and E can be reacted with a molecule containing a terminal alkyne functionality in the presence of a copper(I) catalyst (formed in situ by the reduction of $CuSO_4$ with sodium ascorbate), forming covalently modified monomers G and H.

Scheme 2.

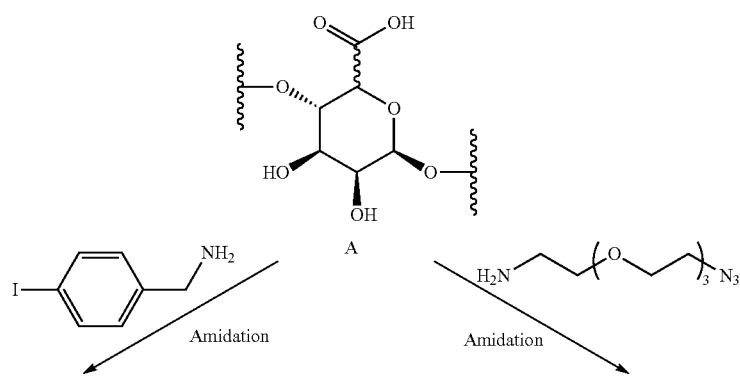

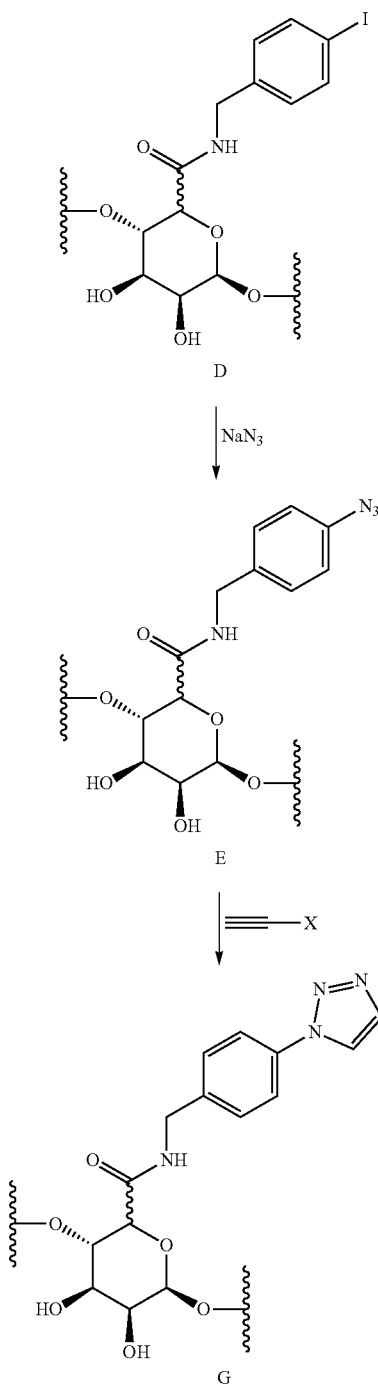
D
↓ NaN₃
E
↓ ≡—X
G
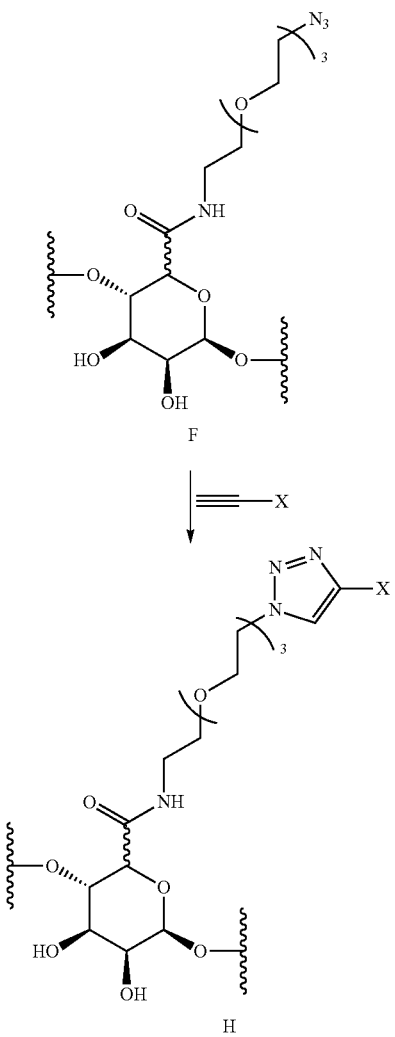
F
↓ ≡—X
H
Preferred alkynes for use as reagents in 1,3-dipolarcycloaddition reactions include those shown below.
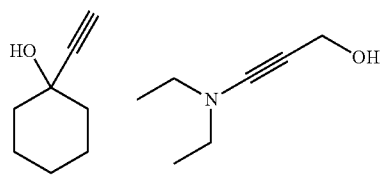
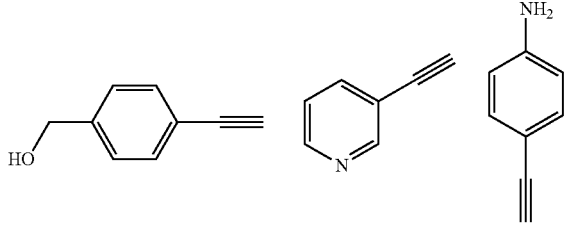

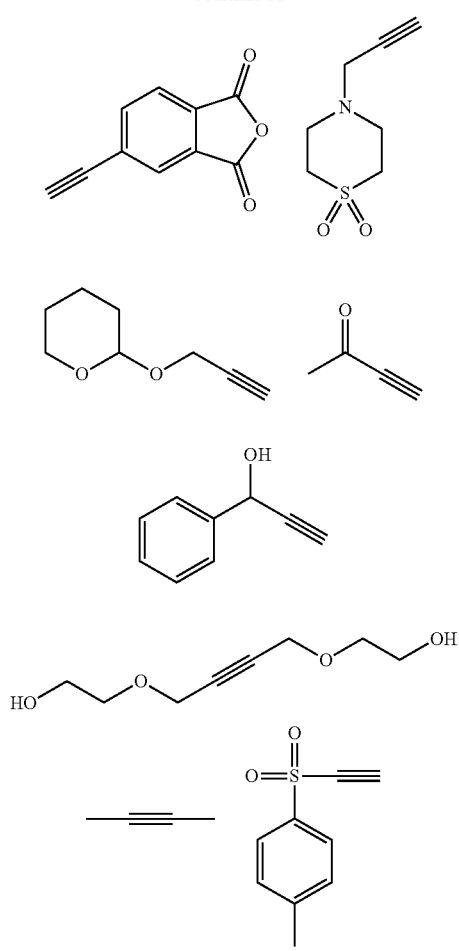
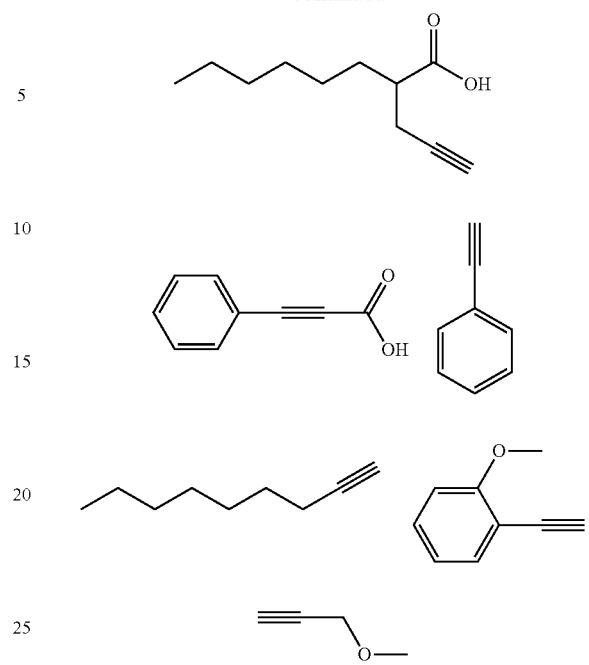
3. Modification Via the Hydroxyl Moiety of the Mannuronate and Guluronate Monomers
Mannuronate and guluronate monomers contain hydroxyl moieties which can serve as a point of covalent modification. In preferred embodiments, the hydroxyl moieties of mannuronate and guluronate residues (1) are reacted as shown in Scheme 3.
Scheme 3.
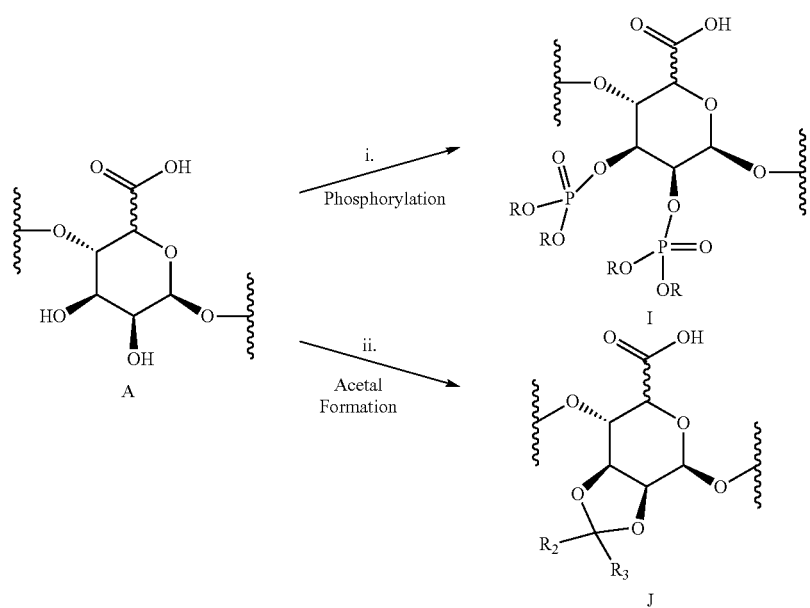

Representative Reaction Conditions: i. I—PO(OR)$_2$, pyridine; ii. R$_2$—CO—R$_3$, H$^+$.

Mannuronate and guluronate residues (A) can be phosphorylated by a variety of methods known in the art, forming covalently modified monomer I. For example, mannuronate and guluronate residues can be phosphorylated by reaction with I—PO(OR)$_2$ in the presence of pyridine (Stowell, 3. K. and Widlanski, T. S. *Tetrahedron Lett.* 1995; 36(11): 1825-1826.

Mannuronate and guluronate residues (A) can also be converted to a cyclic acetal using procedures known in the art. For example, a cyclic acetal can be formed by reaction of mannuronate and guluronate residues with any suitable ketone (R$_2$—CO—R$_3$) in acidic conditions.

4. Methods for Preparing Multiply Modified Alginate Polymers

In the case of singularly modified alginate polymers, only a single reaction or sequence of reactions is performed, introducing one type of covalently modified monomer.

In the case of multiply modified alginate polymers, one or more reactions are performed to introduce multiple different types of covalently modified monomers into the modified alginate polymer. In some embodiments, multiply modified alginate polymers are prepared using multiple sequential synthetic reactions. For example, the multiply modified alginate polymer shown below can be prepared using two sequential reactions: (1) amidation of mannuronate and guluronate monomers with methylamine in the presence of CDMT and NMM; and (2) esterification of mannuronate and guluronate residues with ethanol in the presence of CDMT and NMM.

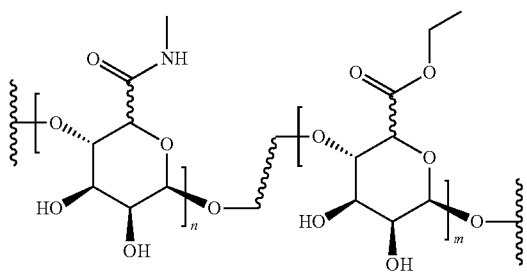

In alternative embodiments, multiply modified alginate polymers can be prepared using a 'one-pot' synthesis. In these embodiments, multiple covalently modified monomers are introduced into the alginate polymer in a single synthetic step. For example, the multiply modified alginate polymer shown above can alternatively be prepared in a single synthetic step by reacting an alginate polymer with methylamine and ethanol in the presence of CDMT and NMM.

C. Purification of Alginates

Commercial alginates are generally obtained from algae. Crude alginates from seaweed contain numerous contaminants, including polyphenols, proteins, and endotoxins (de Vos, P, et al. *Biomaterials* 2006; 27: 5603-5617). The presence of these impurities has been shown to limit the biocompatibility of implanted alginates.

To optimize the biocompatibility of the chemically modified alginates described herein, a rigorous purification methodology was developed to eliminate potentially irritating impurities. In preferred embodiments, ultra-pure low viscosity alginate (UPVLVG, FMC Biopolymer) was used as a substrate for covalent modification. Following each covalent modification, the modified alginates were filtered through modified silica columns, for example cyano-modified silica columns, aimed at capturing bulk organic impurities. Finally, after covalent modification of the alginate polymer is complete, the modified alginates are dialyzed to remove any remaining small-molecule or low molecular weight impurities. In a preferred method, the modified alginates are dialyzed against 10,000 molecular weight cut-off (MWCO) membrane to remove any remaining small-molecule impurities.

The purity of the modified alginates can be determined by $^1$H NMR analysis. In such an analysis, the $^1$H NMR spectra of the modified alginate polymer is collected, and peaks corresponding to the modified alginate polymer and to any impurities are integrated to determine the relative quantity of each species in the sample. In some embodiments, the purity of the modified alginate polymer, as determined by $^1$H NMR, is greater than 90%, 91%, 92%, 93%, 94%, 95%, 96%, 97%, 98%, or 99%. In preferred embodiments, the purity of the modified alginate polymer, as determined by $^1$H NMR, is greater than 90%, more preferably greater than 95%.

III. Assays for the Characterization of Modified Alginate Polymers

The covalent modification of alginate polymers alters the physiochemical properties and biological compatibility of the alginate polymer.

In some embodiments, a hydrogel formation assay is used to quantify the stability of hydrogels formed from alginates or modified alginates. In preferred embodiments, the hydrogel formation assay is used as a screening tool to identify modified alginates capable of forming stable hydrogels.

In vivo assays useful to characterize the biocompatibility of modified alginate polymers. In some embodiments, the high throughput in vivo biocompatibility assay described herein is used to identify modified alginates which induce a lower foreign body response than unmodified alginate.

Further described herein is an in vivo method for quantifying the biocompatibility of modified alginates.

The assays can be used to assess the suitability and biocompatibility of both modified and unmodified alginates for certain applications.

A. High Throughput Hydrogel Formation Assay

Covalent modification of the alginates affects the physical properties of the alginate, including the ability of the alginate to form hydrogels suitable for the encapsulation of cells and biomolecules.

The gel-forming assay exploits the ability of hydrogels to trap fluorescent compounds, and differentially retain the fluorophores upon washing based on the stability of the hydrogel. In this assay, a hydrogel formed by ionically crosslinking a candidate modified alginate in aqueous solution containing a dissolved fluorophore. A variety of fluorophores can be used in this assay. In preferred embodiments, the fluorophores possesses an emission maxima between 480 and 750 nm. In preferred embodiments, the fluorophore is a rhodamine dye possessing an emission maximum between 550 and 600 nm.

After crosslinking, the hydrogel is repeatedly washed with water. Candidate modified alginates which do not efficiently crosslink are washed away along with any fluorophore present. Modified alginates which efficiently crosslink retain the fluorophore during washes. Accordingly, by measuring the fluorescence of modified alginate hydrogels after washing, modified alginates capable of forming stable hydrogels can be readily identified.

In some embodiments, the relative fluorescence intensity values measured for a modified alginate are compared relative to fluorescence levels measured for the negative control and unmodified alginate to determine if the modified alginate is capable of forming hydrogels. In alternative embodiments, the hydrogel formation assay described herein is used to quantify the stability of hydrogels formed from alginates or modified alginates. In these embodiments, the fluorescence intensity measured for a modified alginate is used to indicate the stability of the hydrogel formed by the alginate.

In preferred embodiments, the modified alginate polymer forms hydrogels such that the fluorescence intensity measured using the high throughput hydrogel formation assay described herein is greater than 10,000, 15,000, 20,000, 25,000, 30,000, 35,000, 40,000, 45,000, 50,000, or 55,000. In preferred embodiments, the modified alginate polymer forms hydrogels such that the fluorescence intensity measured using the high throughput hydrogel formation assay described herein is greater than 15,000. In preferred embodiments, the modified alginate polymer forms hydrogels such that the fluorescence intensity measured using the high throughput hydrogel formation assay described herein is between 15,000 and 55,000, more preferably between 25,000 and 55,000.

B. High Throughput In Vivo Biocompatibility Assay

Current biocompatibility analysis methods are slow and require histological analysis. Described herein is a high throughput in vivo biocompatibility assay, useful for assessing the relative biocompatibility of alginate polymers.

In the high throughput in vivo biocompatibility assay described herein, modified alginate polymers and an unmodified alginate control are injected in an array format on the back of an animal test subject to facilitate high-throughput screening. In preferred embodiments, the animal test subject is a mouse. After injection, cathepsin activity at the point of injection of the modified alginates was compared to cathepsin activity at the point of injection the unmodified alginate to compare the foreign body response to the implanted alginates using in vivo fluorescence imaging. In preferred embodiments, the biocompatibility of the materials was assessed at 14 days post injection using in vivo fluorescence imaging.

In preferred embodiments, the high throughput in vivo biocompatibility assay described herein is used to identify modified alginates which induce a lower foreign body response than unmodified alginate. The fluorescence intensity measured at the implantation site of modified alginates was compared with the fluorescence intensity measured at the implantation site of an unmodified alginate. In preferred embodiments, modified alginates exhibiting a smaller fluorescence intensity at the implantation site than the fluorescence intensity measured at the implantation site of an unmodified alginates were qualitatively characterized as biocompatible. Conversely, modified alginates exhibiting a greater fluorescence intensity at the implantation site than the fluorescence intensity measured at the implantation site of an unmodified alginates were characterized as not biocompatible.

The high throughput in vivo biocompatibility assay described above can also be used to characterize the ability of modified alginates to form mechanically stable hydrogels in vivo. In preferred embodiments, the in viva stability of the alginate gels was assessed at 28 days post injection.

In preferred embodiments, modified alginates gels which remained at the site of injection after 28 days were characterized as capable of forming mechanically stable hydrogels in vivo. Conversely, modified alginate gels which were not present at the site of injection after 28 days were deemed to not capable of forming mechanically stable hydrogels in vivo.

C. In Vivo Screening of Modified Alginates to Quantify Biocompatibility

Further described herein is an in viva method for quantifying the biocompatibility of modified alginates.

In this method, a modified alginate polymers is injected on the back of an animal test subject. In preferred embodiments, the animal test subject is a mouse. After injection, cathepsin activity at the point of injection of the modified alginates was measured using in vivo fluorescence assay. In preferred embodiments, the fluorescence assay was conducted at 7 days post injection using in vivo fluorescence imaging. In preferred embodiments, the fluorescence intensity was measured and normalized to the fluorescence response measured using unmodified alginate in order to quantify the biocompatibility of the modified alginates.

In preferred embodiments, the modified alginate polymer induces a lower foreign body response than unmodified alginate (i.e. the fluorescence response normalized to unmodified alginate is less that 100%). In some embodiments, the modified alginate polymer is biocompatible such that the fluorescence response normalized to unmodified alginate measured using the in vivo biocompatibility assay described herein is less than 95%, 90%, 85%, 80%, 75%, 70%, 65%, 60%, 55%, 50%, 45%, or 40%. In preferred embodiments, the modified alginate polymer is biocompatible such that the fluorescence response normalized to unmodified alginate measured using the in vivo biocompatibility assay described herein is less than 75%, more preferably less than 65%, and most preferably less than 50%.

IV. Methods of Use

Alginates are used in a variety of applications in the food, pharmaceutical, cosmetic, agriculture, printing, and textile industries. Alginates are widely employed in the food industry as thickening, gelling, stabilizing, bodying, suspending, and emulsifying agents. Alginates can be used as a matrix to control the delivery of therapeutic, prophylactic, and/or diagnostic agents. Alginates can be incorporated in pharmaceutical compositions as excipients, where they can act as viscosifiers, suspension agents, emulsifiers, binders, and disintigrants. Alginate also used as a dental impression material, component of wound dressings, and as a printing agent. One of ordinary skill in the art will recognize that the modified alginates disclosed herein can be used in any application for which alginates are currently employed.

It is specifically contemplated that modified alginates described herein can be used in applications where improved biocompatibility and physical properties, as compared to commercially available alginates, are preferred.

A. Encapsulation of Cells

Alginate can be conically cross-linked with divalent cations, in water, at room temperature, to form a hydrogel matrix. See, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N+$--VVV--$+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

The preferred anions for cross-linking of polymers containing basic sidechains to form a hydrogel are divalent and trivalent anions such as low molecular weight dicarboxylic acids, for example, terephthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

In a preferred method, cells are encapsulated in a modified alginate polymer. In a preferred embodiment, modified alginate capsules are fabricated from solution of modified alginate containing suspended cells using the encapsulator (such as an Inotech encapsulator). In some embodiments, modified alginate are ionically crosslinked with a polyvalent cation, such as $Ca^{2+}$, $Ba^{2+}$, or $Sr^{2+}$. In particularly preferred embodiments, the modified alginate is crosslinked using $BaCl_2$. In some embodiments, the capsules are further purified after formation. In preferred embodiments, the capsules are washed with, for example, HEPES solution, Krebs solution, and/or RPMI-1640 medium.

Cells can be obtained directed from a donor, from cell culture of cells from a donor, or from established cell culture lines. In the preferred embodiments, cells are obtained directly from a donor, washed and implanted directly in combination with the polymeric material. The cells are cultured using techniques known to those skilled in the art of tissue culture. In the preferred embodiment, the cells are autologous—i.e., derived from the individual into which the cells are to be transplanted, but may be allogeneic or heterologous.

Cell attachment and viability can be assessed using scanning electron microscopy, histology, and quantitative assessment with radioisotopes. The function of the implanted cells can be determined using a combination of the above-techniques and functional assays. For example, in the case of hepatocytes, in vivo liver function studies can be performed by placing a cannula into the recipient's common bile duct. Bile can then be collected in increments. Bile pigments can be analyzed by high pressure liquid chromatography looking for underivatized tetrapyrroles or by thin layer chromatography after being converted to azodipyrroles by reaction with diazotized azodipyrroles ethylanthranilate either with or without treatment with P-glucuronidase. Diconjugated and monoconjugated bilirubin can also be determined by thin layer chromatography after alkalinemethanolysis of conjugated bile pigments. In general, as the number of functioning transplanted hepatocytes increases, the levels of conjugated bilirubin will increase. Simple liver function tests can also be done on blood samples, such as albumin production. Analogous organ function studies can be conducted using techniques known to those skilled in the art, as required to determine the extent of cell function after implantation. For example, islet cells of the pancreas may be delivered in a similar fashion to that specifically used to implant hepatocytes, to achieve glucose regulation by appropriate secretion of insulin to cure diabetes. Other endocrine tissues can also be implanted. Studies using labeled glucose as well as studies using protein assays can be performed to quantitate cell mass on the polymer scaffolds. These studies of cell mass can then be correlated with cell functional studies to determine what the appropriate cell mass is. In the case of chondrocytes, function is defined as providing appropriate structural support for the surrounding attached tissues.

This technique can be used to provide multiple cell types, including genetically altered cells, within a three-dimensional scaffolding for the efficient transfer of large number of cells and the promotion of transplant engraftment for the purpose of creating a new tissue or tissue equivalent. It can also be used for immunoprotection of cell transplants while a new tissue or tissue equivalent is growing by excluding the host immune system.

Examples of cells which can be implanted as described herein include chondrocytes and other cells that form cartilage, osteoblasts and other cells that form bone, muscle cells, fibroblasts, and organ cells. As used herein, "organ cells" includes hepatocytes, islet cells, cells of intestinal origin, cells derived from the kidney, and other cells acting primarily to synthesize and secret, or to metabolize materials. A preferred cell type is a pancreatic islet cell.

The polymeric matrix can be combined with humoral factors to promote cell transplantation and engraftment. For example, the polymeric matrix can be combined with angiogenic factors, antibiotics, antiinflammatories, growth factors, compounds which induce differentiation, and other factors which are known to those skilled in the art of cell culture.

For example, humoral factors could be mixed in a slow-release form with the cell-alginate suspension prior to formation of implant or transplantation. Alternatively, the hydrogel could be modified to bind humoral factors or signal recognition sequences prior to combination with isolated cell suspension.

The techniques described herein can be used for delivery of many different cell types to achieve different tissue structures. In the preferred embodiment, the cells are mixed with the hydrogel solution and injected directly into a site where it is desired to implant the cells, prior to hardening of the hydrogel. However, the matrix may also be molded and implanted in one or more different areas of the body to suit a particular application. This application is particularly relevant where a specific structural design is desired or where the area into which the cells are to be implanted lacks specific structure or support to facilitate growth and proliferation of the cells.

The site, or sites, where cells are to be implanted is determined based on individual need, as is the requisite number of cells. For cells having organ function, for example, hepatocytes or islet cells, the mixture can be injected into the mesentery, subcutaneous tissue, retroperitoneum, properitoneal space, and intramuscular space. For formation of cartilage, the cells are injected into the site where cartilage formation is desired. One could also apply an external mold to shape the injected solution. Additionally, by controlling the rate of polymerization, it is possible to mold the cell-hydrogel injected implant like one would mold clay. Alternatively, the mixture can be injected into a mold, the hydrogel allowed to harden, then the material implanted.

B. Treatment of Diseases or Disorders

Encapsulated cells can be transplanted into a patient in need thereof to treat a disease or disorder. In some embodiments, the encapsulated cells are obtained from a genetically non-identical member of the same species. In alternative embodiments, the encapsulated cells are obtained from a different species than the patient. In preferred embodiments, hormone- or protein-secreting cells are encapsulated and transplanted into a patient to treat a disease or disorder.

In preferred embodiments, the disease or disorder is caused by or involves the malfunction hormone- or protein-secreting cells in a patient. In a preferred embodiment, the disease or disorder is diabetes.

The present invention will be further understood by reference to the following non-limiting examples.

EXAMPLES

Example 1: Combinatorial Synthesis of Chemically Modified Alginates

The determinate parameters governing material biocompatibility are poorly understood. Accordingly, the rational design and synthesis of modified alginates possessing improved biocompatibility is challenging. In an effort to identify modified alginates with improved biocompatibility and physical properties, a combinatorial approach was used to prepare a library of modified alginates possessing a range of covalent modifications.

1. General Combinatorial Strategy

A pool of twelve alcohols, nine amines, two amines used to introduce an azide moiety (one amine containing an azide moiety and one amine containing an iodide moiety to be converted to an azide moiety subsequent to amidation), and nineteen alkynes with a range of different chemical structures, hydrophobicities/hydrophilicities, hydrogen-bonding potentials, and charge states were selected as reagents for the combinatorial synthesis of modified alginates. With the knowledge that impurities present in alginate polymers have been shown to limit the biocompatibility of implanted alginates, ultra-pure, low viscosity alginate (UPLVG, FMC Biopolymers) was selected as a starting material for modification experiments.

Alcohols Used as Reagents for Esterification

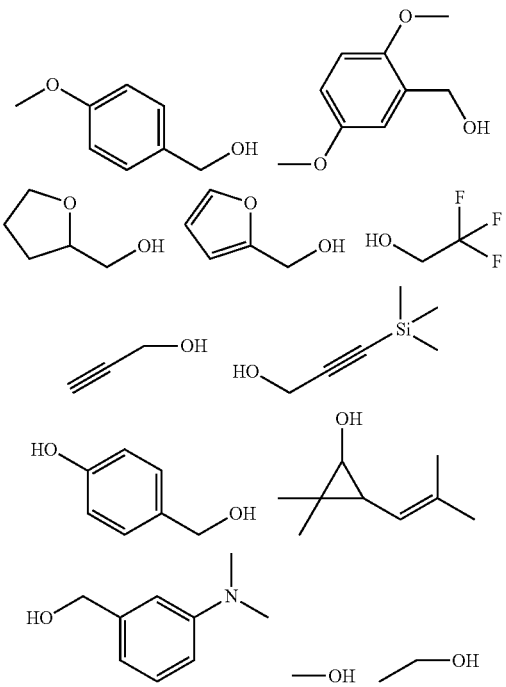

Amines used as Reagents for Amidation

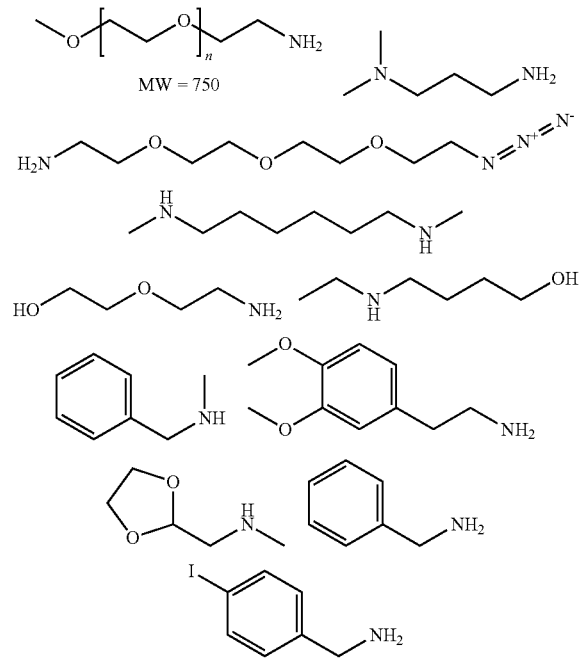

Amines used as Reagents to Introduce Azide Moieties

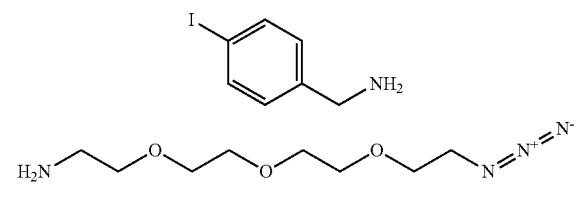

-continued
Alkynes Used as Reagents for 1,3-Dipolar Cycloaddition

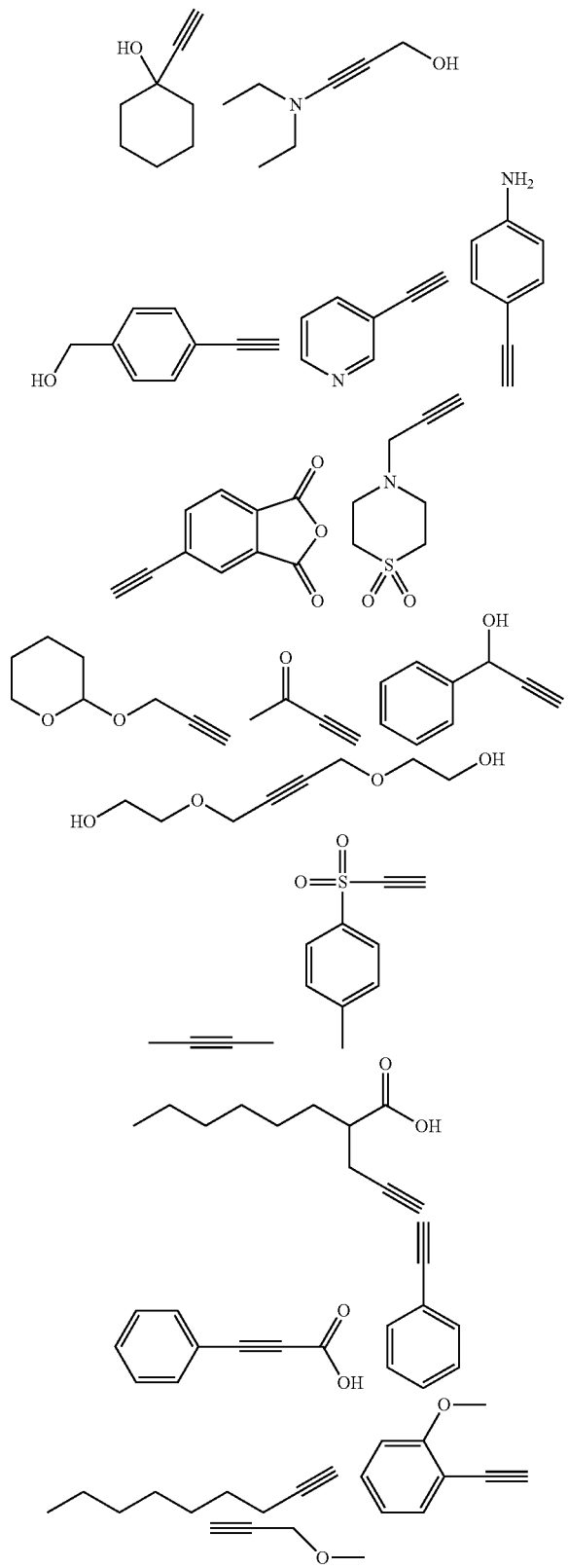

Figure 1:
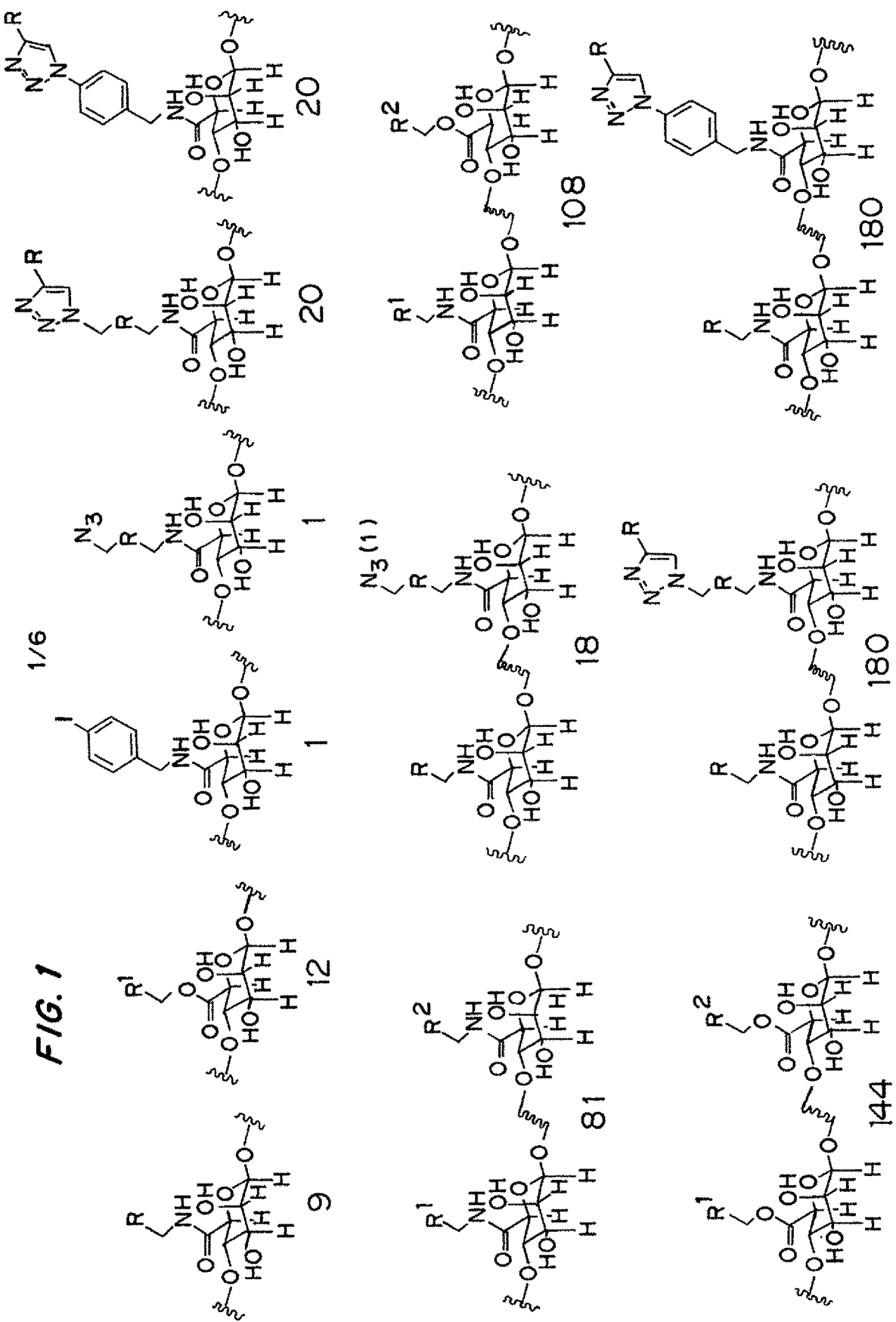
FIG. 1 shows the general structure of the modified alginates obtained using the combinatorial synthetic approach described in Example 1. The number of alginates prepared with each general structure is indicated below.
Figure 2:
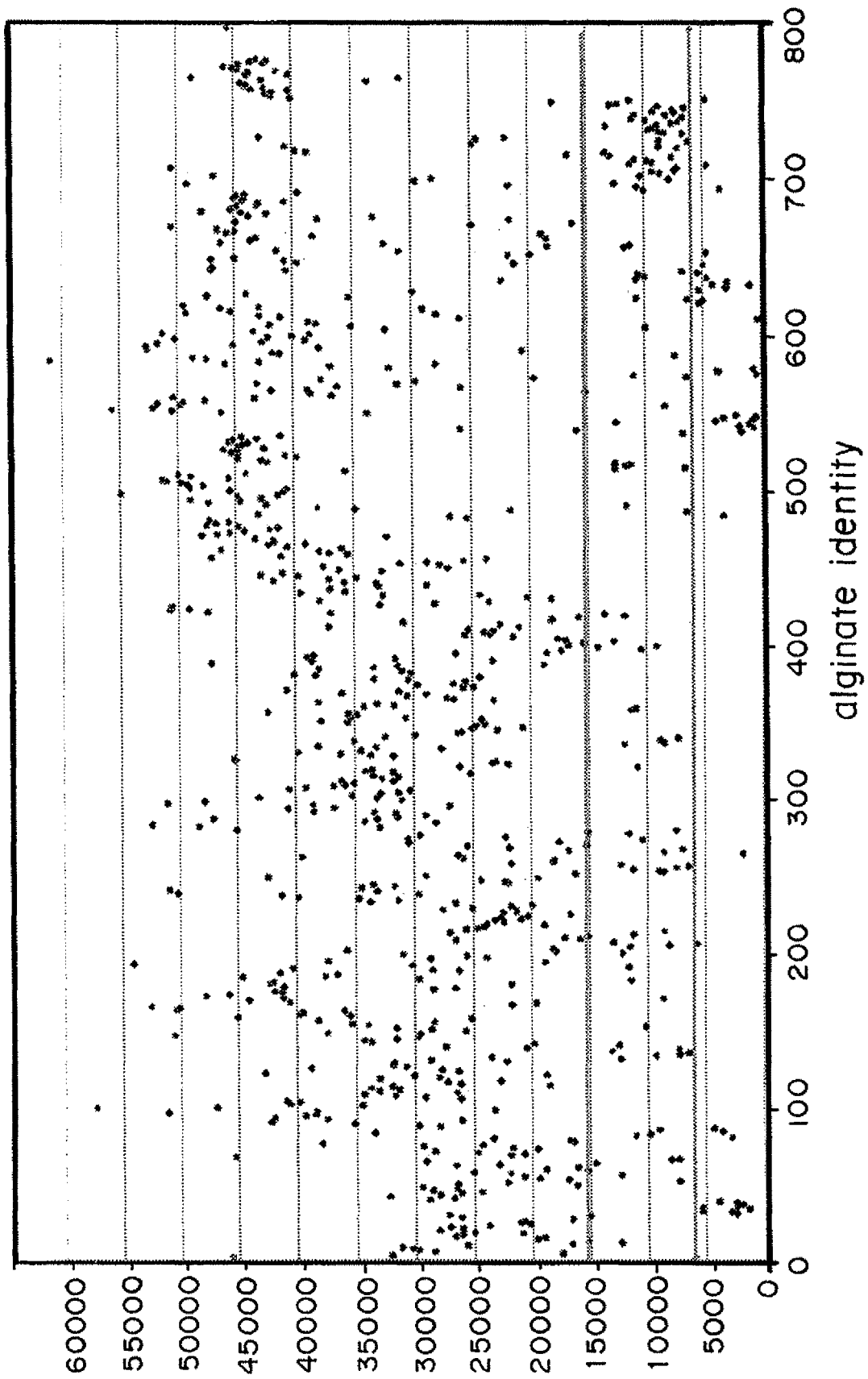
FIG. 2 is a plot obtained from the hydrogel formation assay described in Example 2. The average fluorescence intensity values measured for modified alginates are plotted.

Unmodified alginate polymer was covalently modified by reaction with one, two, or three the esters, amines, and/or alkynes shown above in a combinatorial fashion. FIG. 1 shows the general structure of the modified alginates obtained using this method.

2. Representative Reaction Conditions

Due to the parallel and combinatorial nature of the modification process, synthetic reactions were performed using a robotic core module. UPLVG alginate was selected as a starting material for modification experiments. In the first combinatorial reaction, the unmodified alginate was reacted with one of the alcohols, amines, and amines used to introduce an azide moiety in the presence of 2-Chloro-4,6-dimethoxy-1,3,5-triazine (CDMT) and N-methyl morpholine (NMM). In a second combinatorial step, each of the modified alginate polymers formed above was reacted with another of the alcohols, amines, or amines used to introduce an azide moiety in the presence of 2-Chloro-4,6-dimethoxy-1,3,5-triazine (CDMT) and N-methyl morpholine (NMM). In a final combinatorial step, all members of the library which were reacted with an amine used to introduce an azide moiety were further functionalized using a 1,3-dipolar cycloaddition reaction. Those members of the library which had been reacted with 4-iodobenzylamine were first reacted with sodium azide to convert the iodide moieties to azide moieties. Subsequently, all members of the library which were reacted with an amine used to introduce an azide moiety were reacted with one of the alkynes used as reagents for 1,3-dipolar cycloaddition in the presence of $CuSO_4$/sodium ascorbate.

To optimize the biocompatibility of the chemically modified alginates, a rigorous purification methodology was developed to eliminate potentially irritating impurities. Following each covalent modification, the modified alginates were filtered through a cyano-modified silica column aimed at capturing bulk organic impurities. Finally, after completing all covalent modification steps, the modified alginates were dialyzed against 10,000 MWCO membrane to remove any remaining small-molecule or low molecular weight impurities.

The purity of the modified alginates was determined by $^1$H NMR analysis. The $^1$H NMR spectra of each modified alginate polymer was collected, and peaks corresponding to the modified alginate polymer and to any impurities were integrated to determine the relative quantity of each species in the sample.

Example 2: High Throughput Screening of Modified Alginates Using a Hydrogel Formation Assay Covalent modification of the alginates affects the physical properties of the alginate, including the ability of the alginate to form hydrogels suitable for the encapsulation of cells and biomolecules. To eliminate modified alginates that have lost their ability to form hydrogels and to further focus our screening efforts on stronger candidates, a fluorescence-based crosslinking assay was used to quantify the ability of modified alginates to form hydrogels.

The hydrogel formation assay described herein exploits the ability of hydrogels to trap fluorescent compounds, and differentially retain the fluorophores upon washing based on the stability of the hydrogel. Each of the modified alginates prepared using the combinatorial approach described in Example 1 was dissolved in water. A rhodamine dye that fluoresces at 580 nm was added to each sample. The modified alginate sample was then crosslinked by the addition of a barium or calcium salt, for example $BaCl_2$, to induce formation of a hydrogel. After incubation for 10 minutes, each sample was washed repeatedly with water. The fluorescence intensity of each sample was measured using a fluorimeter.

Each modified alginate was screened three times, and the results obtained in the three trials were averaged. The average fluorescence intensity values for each modified alginate were compared to the fluorescence levels of the negative control (water) and unmodified alginate (UPLVG). Modified alginates yielding fluorescence values below the negative control were considered unusable for applications where hydrogel formation is critical (i.e. the encapsulation of cells).

Example 3: In Vitro Screening of Modified Alginates for Biocompatibility

The cytotoxicity of the modified alginate polymers on HeLa cells was evaluated to screen for biocompatibility in vitro. The modified alginates identified in Example 2 as capable of forming hydrogels were loaded into wells of 96-well plates which were coated with poly-L-lysine. Unmodified alginate and saline were also loaded into wells of 96-well plates which were coated with poly-L-lysine as controls. A 100 mM $BaCl_2$ crosslinking solution was dispensed in all of the wells of the 96-well plate. The excess crosslinker was then aspirated. HeLa cells were seeded into the wells and incubated for 3 days at 37° C. in a humidified chamber.

A cell viability assay using 3-(4,5-Dimethylthiazol-2-yl)-2,5-diphenyltetrazolium bromide (MTT) was performed, in which the media was aspirated from all wells and 100 µl of DMEM media without phenol red and 100 MTT (5 mg/ml) were added to all of the wells of the 96-well plate. The plate was incubated for 4 hours at 37° C. in a humidified chamber. After incubation, 85 µl of solution was aspirated and 100 µl DMSO was added. Purple formazan crystals form during the assay in proportion to the number of viable HeLa cells present in each well. The contents of each well were pipetted up and down to solubilize the formazan crystals prior to measurement. The plate was incubated at 37° C. for 10 minutes after which the bubbles from agitation were removed. The plate was read using a UV/Vis plate reader at 540 nm with a reference at 700 nm. The viability was normalized to cells seeded in wells with no alginate.

The results of the cell viability are shown in FIG. 3, which plots the effect of selected modified alginates on HeLa cell line viability as compared to the positive control (no alginate). Alginate (Alg) has a viability of 53%. The assay identified modified alginate polymers which displayed decreased cytotoxicity relative to unmodified alginate. These were selected for further analysis.

Example 4: High Throughput In Vivo Screening of Modified Alginates to Assess Biocompatibility Current biocompatibility analysis methods are slow and require histological analysis. In order to screen the large numbers of modified alginates prepared using the combinatorial synthetic methods described herein, a high throughput in vivo biocompatibility assay was used to assess the relative biocompatibility of alginate polymers.

1. High Throughput In Vivo Screening Protocol 8-12 week old male SKH1 mice were obtained from Charles River Laboratories (Wilmington, Mass.). The mice were maintained at the animal facilities of Massachusetts Institute of Technology, accredited by the American Association of Laboratory Animal care, and were housed under standard conditions with a 12-hour light/dark cycle. Both water and food were provided ad libitum.

Injections were performed in accordance with ISO 10993-6: 2001. Prior to injection all materials were sterilized via 0.22 µm filtration. The mice were anesthetized via isoflurane inhalation at a concentration of 1-4% isoflurane/balance $O_2$ to minimize movement. Their backs were scrubbed with 70% isopropyl alcohol and the animals were injected with modified alginates in an array format on the mouse's back for high-throughput screening. Six injections were made in each mouse with one of the injections being an unmodified alginate control. Injection volumes were 100 µl.

On days 1, 3, 7, 14, 21, and 28 post injection, host cell activity in response to the implantation of modified alginates was imaged kinetically using fluorescent whole animal imaging. 24 hours before in vivo fluorescence imaging, 2 nmol of ProSense-680 (VisEn Medical, Woburn, Mass., excitation wavelength 680±10 nm, emission 700±10 nm) dissolved in 150 µl sterile PBS was injected into the tail vein of each mouse to image cathepsin activity.

In vivo fluorescence imaging was performed with an IVIS-Spectrum measurement system (Xenogen, Hopkinton, Mass.). The animals were maintained under inhaled anesthesia using 1-4% isoflurane in 100% oxygen at a flow rate of 2.5 L/min. A binning of 8×8 and a field of view of 13.1 cm were used for imaging. Exposure time and f/stop the relative size of the opening of the aperture—were optimized for each acquired image. Data were acquired and analyzed using the manufacturer's proprietary Living Image 3.1 software. All images are presented in fluorescence efficiency, which is defined as the ratio of the collected fluorescent intensity to an internal standard of incident intensity at the selected imaging configuration. Regions of interest (ROIs) were designated around the site of each injection.

Biocompatibility of the materials was examined 14 days post injection. The fluorescence intensity measured at the implantation site of modified alginates was compared with the fluorescence intensity measured at the implantation site of and unmodified alginates. Modified alginates exhibiting a smaller fluorescence intensity at the implantation site than the fluorescence intensity measured at the implantation site of an unmodified alginates were characterized as biocompatible. Modified alginates exhibiting a greater fluorescence intensity at the implantation site than the fluorescence intensity measured at the implantation site of an unmodified alginates were characterized as not biocompatible.

The in vivo stability of the alginate gels was assessed at 28 days post injection. Modified alginates which remained at the site of injection after 28 days were characterized as capable of forming mechanically stable hydrogels in vivo. Modified alginates which were not present at the site of injection after 28 days were deemed to not capable of forming mechanically stable hydrogels in vivo, and were classified as 'failures'.

Modified alginates characterized as both biocompatible and capable of forming mechanically stable hydrogels in vivo were identified as 'hits', and selected for further study.

2. Validation of the High Throughput In Vivo Screening Protocol

In order to validate the high throughput in vivo screening assay described above, modified alginates were subcutaneously injected into mice in an array format and crosslinked in situ as described above. Mice were imaged on days 1, 3, 7, 14, 21, and 28 post injection using fluorescent whole animal imaging, and tissue samples were collected after imaging for histological analysis. To obtain tissue samples for histological analysis, mice were euthanized via $CO_2$ asphyxiation and the injected biomaterial and surrounding tissue were excised. The tissues were then fixed in 10% formalin, embedded in paraffin, cut into 5 µm sections, and stained using hematoxylin and eosin (H&E) for histological analysis by a board certified pathologist.

Fibrosis was rated on a scale where a zero involved no fibrosis, a one indicated partial coverage with one to two layers of fibrosis, a two is designated a thicker fibrotic layer that nearly covered the implant, and a three denoted concentric fibrotic coverage of the polymer. Both polymorphonuclear (PMN) cells and macrophages were rated on a scale where no observed cells were indicated with a zero, scattered cells scored a one, numerous cells clustering on the sides of the polymer scored a two, and numerous cells surrounding the material resulted in a three. Both the histological score and fluorescence response normalized to alginate were examined for the whole library and materials that outperformed unmodified alginate were judged to be biocompatible. This corresponds to a normalized fluorescent signal of <100% and a fibrosis score of <3.

Data captured using whole animal imaging was demonstrated to displayed similar temporal trends in cellular recruitment of phagocytes to the biomaterials compared to histological analysis. Accordingly, the high throughput in vivo screening method described above was validated.

Example 5: In Vivo Screening of Modified Alginates to Quantify Biocompatibility 8-12 week old male SKH1 mice were obtained from Charles River Laboratories (Wilmington, Mass.). The mice were maintained at the animal facilities of Massachusetts Institute of Technology, accredited by the American Association of Laboratory Animal care, and were housed under standard conditions with a 12-hour light/dark cycle. Both water and food were provided ad libitum.

Injections were performed in accordance with ISO 10993-6: 2001. Prior to injection all materials were sterilized via 0.22 μm filtration. The mice were anesthetized via isoflurane inhalation at a concentration of 1-4% isoflurane/balance $O_2$ to minimize movement. Their backs were scrubbed with 70% isopropyl alcohol and the animals were injected with a modified alginate. The injection volume was 100 μl.

Cathepsin activity was measured 7 days post injection using an in vivo fluorescence assay to quantify the foreign body response to the modified alginate. 24 hours before in vivo fluorescence imaging, 2 nmol of ProSense-680 (VisEn Medical, Woburn, Mass., excitation wavelength 680±10 nm, emission 700±10 nm) dissolved in 150 μl sterile PBS was injected into the tail vein of each mouse to image cathepsin activity.

In vivo fluorescence imaging was performed with an IVIS-Spectrum measurement system (Xenogen, Hopkinton, Mass.). The animals were maintained under inhaled anesthesia using 1-4% isoflurane in 100% oxygen at a flow rate of 2.5 L/min. A binning of 8×8 and a field of view of 13.1 cm were used for imaging. Exposure time and f/stop—the relative size of the opening of the aperture—were optimized for each acquired image. Data were acquired and analyzed using the manufacturer's proprietary Living Image 3.1 software. All images are presented in fluorescence efficiency, which is defined as the ratio of the collected fluorescent intensity to an internal standard of incident intensity at the selected imaging configuration. Regions of interest (ROIs) were designated around the site of each injection.

Fluorescence images were captured 7 days post-injection illustrating relative cathepsin activity at the point of injection of selected modified alginates. The fluorescence intensity was measured and normalized to the fluorescence response measured using unmodified alginate in order to quantify the biocompatibility of the modified alginates. The results obtained for selected modified alginates are included in FIG. 4.

Example 6: Treatment of Diabetes in STZ-Induced Diabetic Mice

The transplantation of biocompatible alginate-encapsulated beta cells offers potential as a treatment for diabetes. Pancreatic rat islet cells were encapsulated using fourteen biocompatible modified alginate polymers identified using the assays detailed above (including PF_N287_B_B4, PF_N287_F2, PF_N287_G3, PF_N287_B3, PF_N287_B_B8, PF_N287_A4, PF_N287_B1, PF_N287_E3, PF_N263_C12, PF_N63_A12, PF_N287_E1, PF_N287_D3, PF_N263_A7, and PF_N263_C6). Alginate-encapsulated islets capsules were fabricated from 750 μl of a 4% (w/v) solution of each modified alginate in deionized water containing suspended 1,000 islets suspended using the Inotech encapsulator (Inotech) set to a voltage of 1.05 kV, a vibration of 1225 Hz, and a flow rate of 10-25 ml/min with a 300 μm nozzle. Alginate was crosslinked in a 20 mM $BaCl_2$ solution. After encapsulation, the capsules were washed twice with HEPES solution, four times with Krebs solution, and twice with RPMI-1640 medium.

The encapsulated rat islet cells were transplanted into STZ induced diabetic mice. Prior to transplantation, the mice were anesthetized under continuous flow of 1-4% isofluorane with oxygen at 0.5 L/min. A shaver with size #40 clipper blade will be used to remove hair to reveal an area of about 2 cm×2 cm on ventral midline of the animal abdomen. The entire shaved area was aseptically prepared with a minimum of 3 cycles of scrubbing with povidine, followed by rinsing with 70% alcohol. A final skin paint with povidine was also applied. The surgical site was draped with sterile disposable paper to exclude surrounding hair from touching the surgical site. A sharp surgical blade was used to cut a 0.5-0.75 cm midline incision through the skin and the linea alba into the abdomen. A sterile plastic pipette was used to transfer the alginate microcapsules into the peritoneal cavity. The abdominal muscle was closed by suturing with 5-0 Ethicon black silk or PDS-absorbable 5.0-6.0 monofilament absorbable thread. The external skin layer was closed using wound clips. These wound clips were removed 7-10d post-surgery after complete healing was confirmed.

Blood glucose levels in the STZ induced diabetic mice were monitored daily for between 20 and 30 days post-transplantation using a drop of blood obtained by scrubbing the tail with 70% isopropyl alcohol and making a superficial cut on the skin of the tail to produce a drop of blood. Mice were restrained during sampling in a rotating tail injector.

The blood glucose levels in the STZ induced diabetic mice following islet transplantation are shown in FIG. 5. The dashed black line represents normoglycemia in mice. Pancreatic rat islet cells were encapsulated in modified alginates were able to reduce the blood glucose levels in all cases, and in some cases, were even able to induce normoglycemia.

Example 7. Particles Prepared from Mixture of Modified Alginate(s) and Unmodified Alginate The growing recognition of the parameters driving fibrosis in vivo has been applied to the analysis of the performance of modified alginates. Intraperitoneal (IP) implantation of modified alginate capsules revealed that modified alginates may result in abnormally shaped capsules when crosslinked using conditions defined for unmodified alginates. These abnormally shaped capsules can complicate implementation and interpretation of modified alginate capsules implanted IP. In an effort to improve the capsule morphology, formulation methods for use with modified alginate microparticles were developed where modified alginates were blended with a small amount of high molecular weight alginate. Particles prepared from this mixture yielded particles with improved morphology and stability.

A 6% solution of modified alginate (w/w) was combined 1:1 by volume with a 1.15% solution of unmodified alginate (w/w). After mixing, capsules are formed by following this solution through an electrostatic droplet generator, followed by crosslinking of the polymer in a 20 mM aqueous barium chloride solution.

Particles prepared from modified alginate 263_A12 microparticles formulated with barium and mannitol were compared to particles prepared from 263_A12 blended with a small amount of unmodified SLG100 alginate (16% by weight). The particles prepared from a mixture of modified alginate and unmodified alginate produced more homogenous microparticle populations. Quantitative fluorescence analysis with prosense at several time points with modified alginates blended with SLG100 was performed. The results are shown in FIG. 6. Several reformulated modified alginates displayed less inflammatory response at day 7 compared to the control alginate. Initial experiments with large capsules (1.5 mm diameter) show comparably clean capsules after 2 weeks in the IP space of immunocompetent C57BL6 mice.

Data collected to date with these controlled capsules indicates that reformulation and capsule morphology can have a significant effect on inflammation as measured by prosense. An improved inflammation response is observed in some polymers (FIG. 6), while others are impacted negatively.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A multiply modified alginate polymer which is selected from

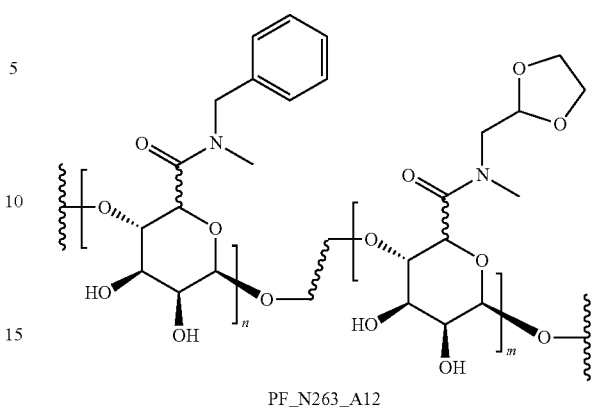

PF_N263_A12

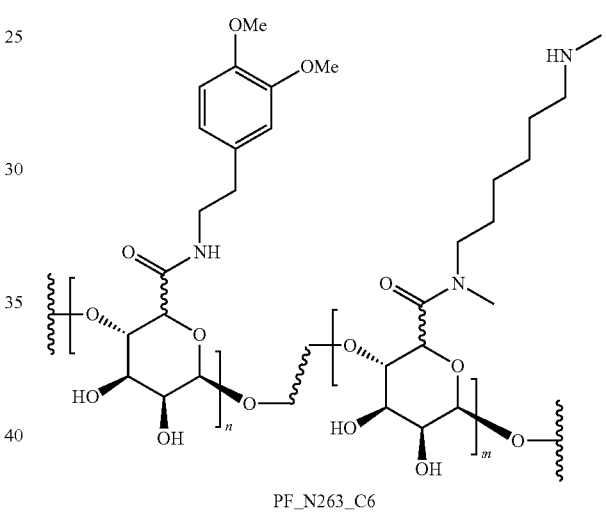

PF_N263_C6

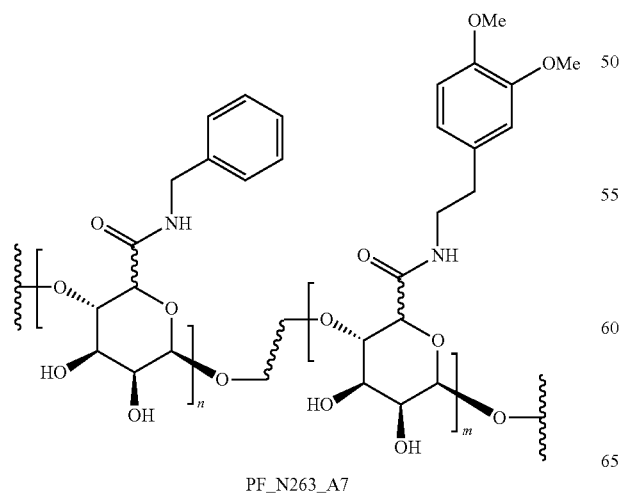

PF_N263_A7

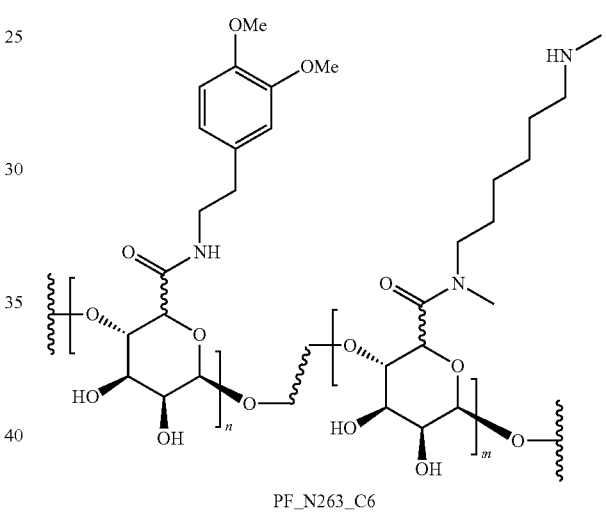

PF_N263_C12

-continued

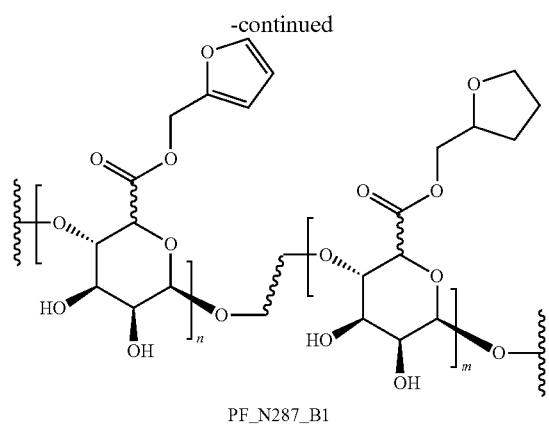

PF_N287_B1

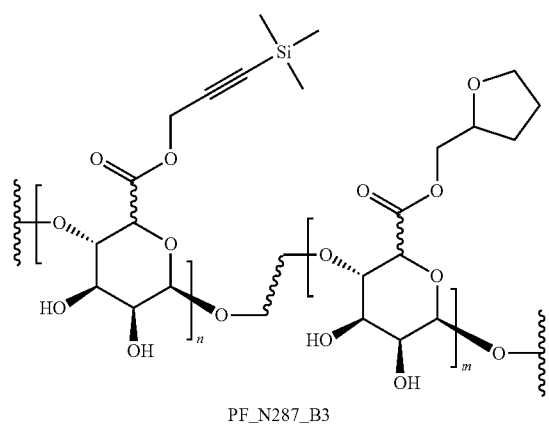

PF_N287_B3

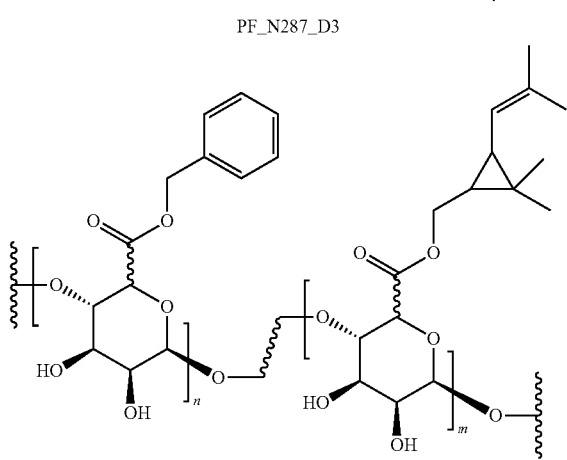

PF_N287_D3

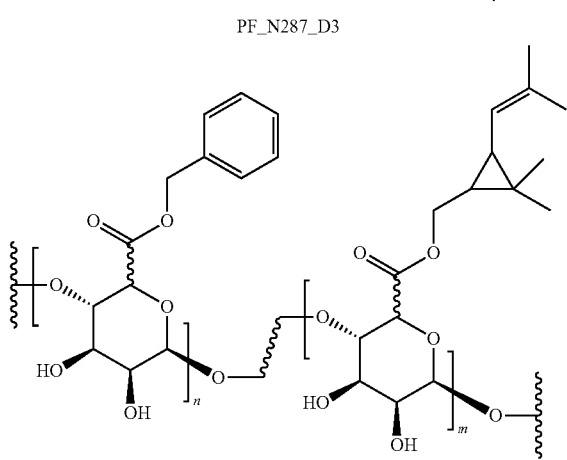

PF_N263_E1
and

-continued

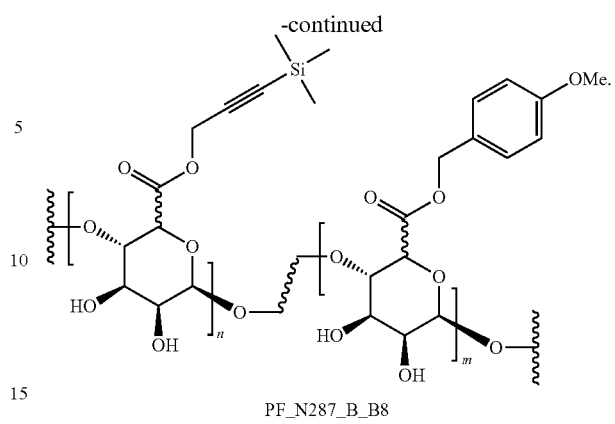

PF_N287_B_B8

2. The multiply modified alginate polymer of claim 1, wherein more than 15% of the monomers in the modified alginate polymer are covalently modified monomers.

3. The multiply modified alginate polymer of claim 1, which is

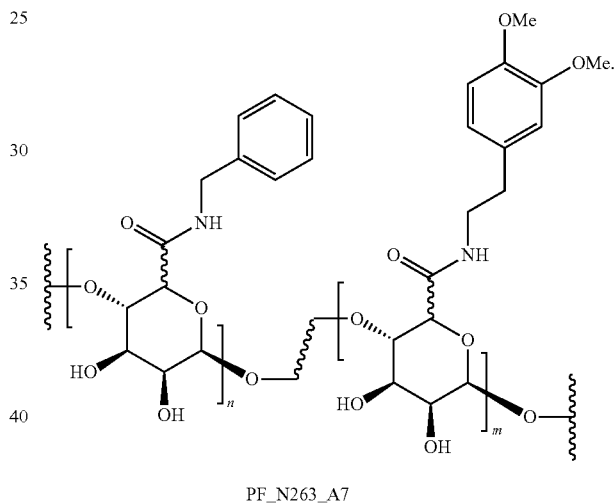

PF_N263_A7

4. The multiply modified alginate polymer of claim 1, which is

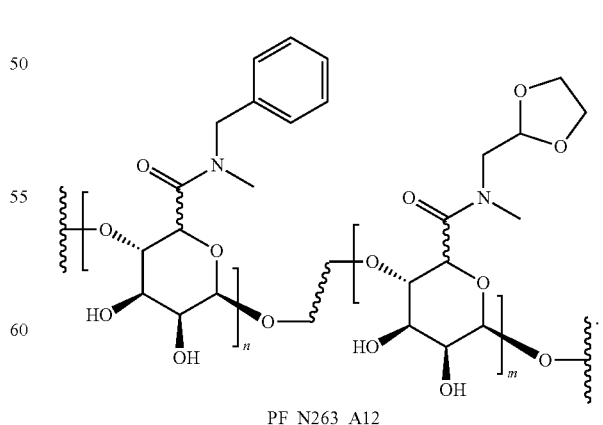

PF_N263_A12

5. The multiply modified alginate polymer of claim 1, which is

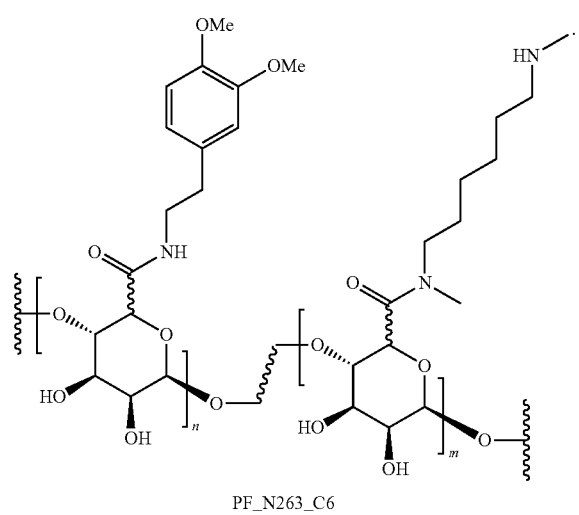

PF_N263_C6

6. The multiply modified alginate polymer of claim 1, which is

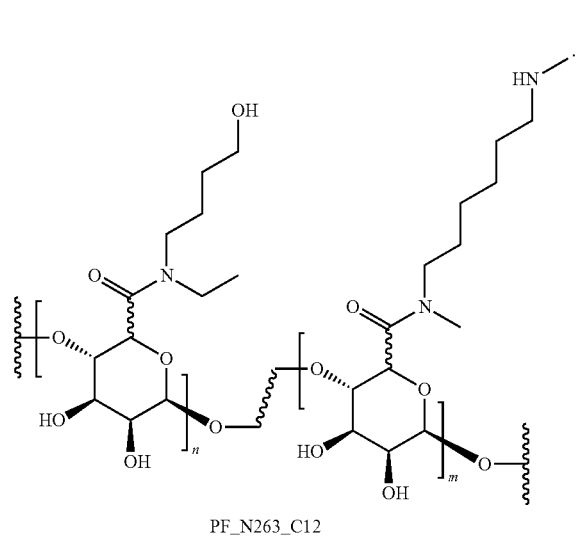

PF_N263_C12

7. The multiply modified alginate polymer of claim 1, which is

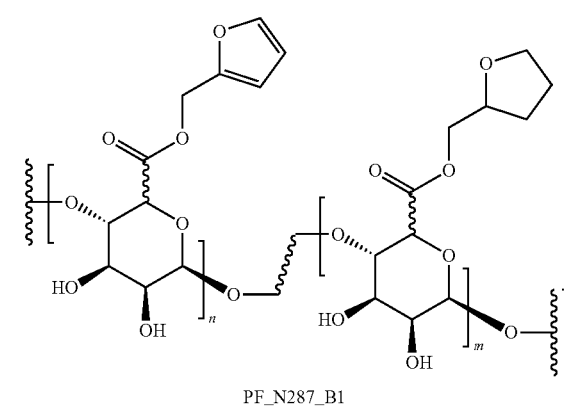

PF_N287_B1

8. The multiply modified alginate polymer of claim 1, which is

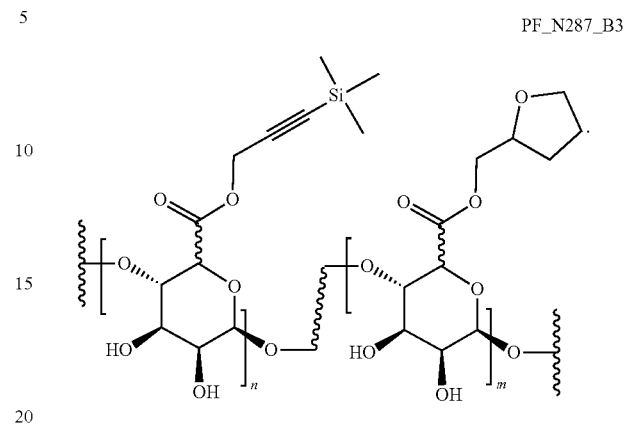

PF_N287_B3

9. The multiply modified alginate polymer of claim 1, which is

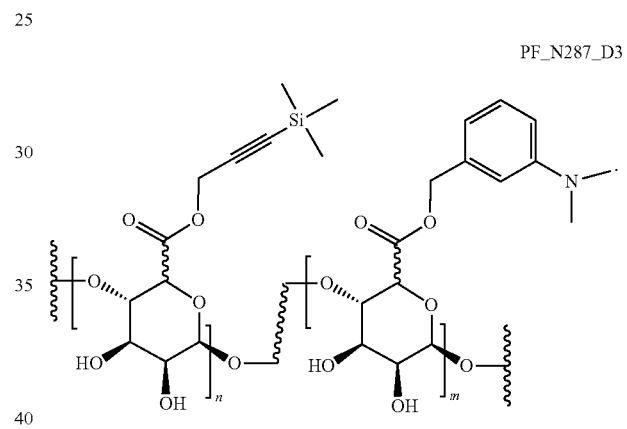

PF_N287_D3

10. The multiply modified alginate polymer of claim 1, which is

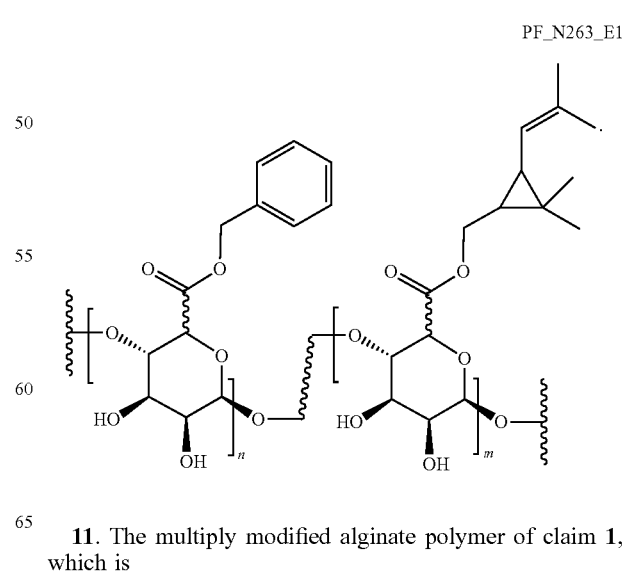

PF_N263_E1

11. The multiply modified alginate polymer of claim 1, which is

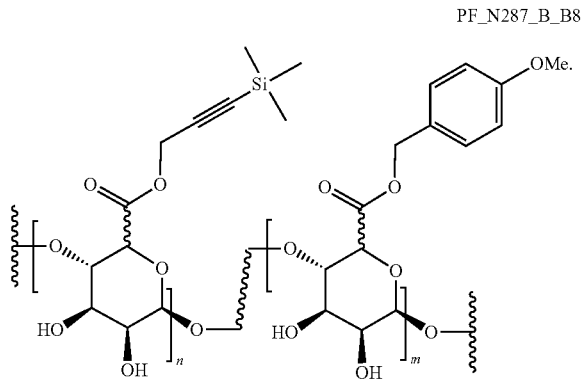

PF_N287_B_B8

12. A hydrogel comprising a modified alginate according to claim 1.

13. The hydrogel of claim 12, comprising Ca$^{2+}$, Ba$^{2+}$, or Sr$^{2+}$ crosslinking the modified alginate polymer.

14. The hydrogel of claim 12, wherein the multiply modified alginate polymer is

15. A capsule comprising a hydrogel according to claim 12 and having cells encapsulated therein.

16. The capsule of claim 15, wherein the hydrogel further comprises an unmodified alginate.

17. The capsule of claim 16, wherein the unmodified alginate has a weight average molecular weight of 50,000 to 250,000 Daltons.

18. The capsule of claim 15, wherein the cells are genetically altered.

19. The capsule of claim 15, wherein the cells are islet cells.

20. The capsule of claim 15, wherein the multiply modified alginate polymer is

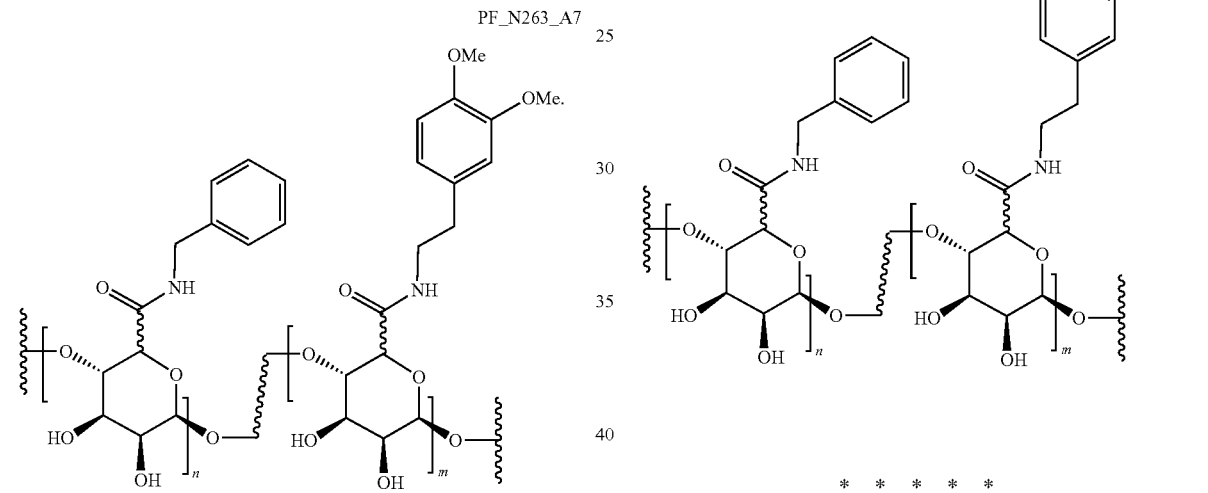

PF_N263_A7

* * * * *